(12) United States Patent
Khodja et al.

(10) Patent No.: US 11,415,501 B2
(45) Date of Patent: Aug. 16, 2022

(54) METHOD OF DETERMINING ABSOLUTE PERMEABILITY

(71) Applicant: KING FAHD UNIVERSITY OF PETROLEUM AND MINERALS, Dhahran (SA)

(72) Inventors: Mohamed R. Khodja, Dhahran (SA); Jun Li, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 446 days.

(21) Appl. No.: 16/654,474

(22) Filed: Oct. 16, 2019

(65) Prior Publication Data

US 2021/0116354 A1    Apr. 22, 2021

(51) Int. Cl.
*G01N 15/08* (2006.01)
*G01N 33/24* (2006.01)
(Continued)

(52) U.S. Cl.
CPC ......... *G01N 15/0886* (2013.01); *G01N 15/02* (2013.01); *G01N 24/08* (2013.01);
(Continued)

(58) Field of Classification Search
CPC ........ G01N 15/00; G01N 15/02; G01N 15/08; G01N 15/0886; G01N 24/08; G01N 33/24; G01N 2015/0813; G01N 2015/0846
See application file for complete search history.

(56) References Cited

U.S. PATENT DOCUMENTS 9,046,509 B2 *   6/2015   Dvorkin ............... G06T 7/0004
10,656,068 B2 *  5/2020   León Carrera ........ G01N 15/08
(Continued)

FOREIGN PATENT DOCUMENTS

CN    104866706 A    8/2015

OTHER PUBLICATIONS

Hua Dong, et al., "Relationship between the Size of the Samples and the Interpretation of the Mercury Intrusion Results of an Artificial Sandstone", Materials, vol. 11, No. 201, Jan. 27, 2018, pp. 1-17.
(Continued)

*Primary Examiner* — Nguyen Q. Ha
(74) *Attorney, Agent, or Firm* — Oblon, McClelland, Maier & Neustadt, L.L.P.

(57) ABSTRACT

A method of determining absolute permeability in carbonates without upscaling computations includes performing a nuclear magnetic resonance (NMR) analysis and a mercury-injection capillary-pressure (MICP) analysis on at least three samples from carbonate rock of a set of representative regions to determine an experimental permeability, where each of the representative regions have properties related to the porosity and pore-throat size of the carbonate rock. A series of low resolution X-ray scans and a series of high resolution X-ray scans are performed on the same three samples of the carbonate rock of the set of representative regions. Permeability simulations are performed on the same three samples of the carbonate rock of the set of representative regions to determine a computed permeability. The experimental permeability and the computed permeability are then compared to provide computationally manageable and reasonable estimates of the absolute permeability of the carbonate rock.

14 Claims, 17 Drawing Sheets

(51) Int. Cl.
*G01N 15/02* (2006.01)
*G01N 24/08* (2006.01)
(52) U.S. Cl.
CPC ..... *G01N 33/24* (2013.01); *G01N 2015/0813* (2013.01); *G01N 2015/0846* (2013.01)

(56) References Cited

U.S. PATENT DOCUMENTS

2011/0004448 A1    1/2011   Hurley et al.
2012/0221306 A1    8/2012   Hurley et al.

OTHER PUBLICATIONS

Amina Islam, et al., "Multi-scale experimental and numerical simulation workflow of absolute permeability in heterogeneous carbonates", Journal of Petroleum Science and Engineering, vol. 173, 2019, pp. 326-338.

Huafeng Sun, et al., "Rock properties evaluation for carbonate reservoir characterization with multi-scale digital rock images", Journal of Petroleum Science and Engineering, vol. 175, Apr. 2019, pp. 654-664 (Abstract Only).

\* cited by examiner

METHOD OF DETERMINING ABSOLUTE PERMEABILITY

STATEMENT OF ACKNOWLEDGEMENT

The support provided by King Fahd University of Petroleum and Minerals is gratefully acknowledged.

BACKGROUND

Field of the Invention

The present disclosure relates to a method and system of predicting, determining, characterizing and/or identifying absolute permeability of reservoir carbonate rocks. The method of the present disclosure describes selecting an appropriate subdomain of a carbonate reservoir rock such that upscaling computations may be avoided when determining the permeability of a carbonate rock.

Description of the Related Art

Studies estimate that more than half of the worlds proven conventional oil reserves and more than one third of the world's proven gas reserves are in the Middle East. Approximately, 60% of the world's oil reserves and 90% of the gas reserves reside in carbonate reservoirs. Production from these reservoirs is challenging since carbonates are characterized by a wide variety of petrophysical and flow properties that are oftentimes found in small scales or domains. Understanding how these multimodal small-scale heterogeneities affect the performance of the reservoir is a fundamental and challenging problem that requires the integration of a multitude of multidisciplinary studies. Carbonates are known to exhibit complex pore networks, wherein the structure of the pore networks has a considerable effect on fluid flow and other carbonate related properties. See A. Moctezuma-Berthier, O. Vizika, J. F. Thovert, and P. M. Adler. One- and two-phase permeabilities of vugular porous media. *Transport in Porous Media*, 56:225-244, 2004; S. Norouzi Apourvari and C. H. Arns. Image-based relative permeability upscaling from the pore scale. *Advanced Water Resources*, 95:16-175, 2015; and F. Gjetvaj, A. Russian, P. Gouze, and M. Dentz. Dual control of flow field heterogeneity and immobile porosity on non-fickian transport in berea sandstone. *Water Resources Research*, 51:8273-8293, 2015, each incorporated herein by reference in their entirety.

Generally, petrophysical properties of reservoir rock are obtained by performing a variety of experimental tests on actual core samples. These tests are costly, time-consuming, and destructive. Digital rock physics (DRP) has emerged as a powerful and attractive methodology that complements conventional core analysis since digital rock analysis is carried out on digitized models of the core. See J. Dvorkin, M. Armbruster, C. Baldwin, and Q. Fang. The future of digital rock physics: computational methods vs. lab testing. First Break, 26:6368, 2008; M. Z. Kalam. *New Technologies in the Oil and Gas Industry*, chapter Digital Rock Physics for Fast and Accurate Special Core Analysis in Carbonates, pages 201-226. INTECH Open Access, 2012; H. Andra, N. Combaret, J. Dvorkin, E. Glatt, J. Han, M. Kabel, Y. Keehm, F. Krzikalla, M. Lee, C. Madonna, M. Marsh, T. Mukerji, E. Saenger, R. Sain, N Saxena, S. Ricker, A. Wiegmann, and X. Zhan. Digital rock physics benchmarks part I: Imaging and segmentation. *Computers & Geosciences*, 50:25-32, 2013; H. Andraa, N. Combaret, J. Dvorkin, E. Glatt, J. Han, M. Kabel, Y. Keehm, F. Krzikalla, M. Lee, C. Madonna, M. Marsh, T. Mukerji, E. Saenger, R. Sain, N Saxena, S. Ricker, A. Wiegmann, and X. Zhan. Digital rock physics benchmarks part II: Computing effective properties. *Computers & Geosciences*, 50:33-43, 2013; and V. Cnudde and M. N. Boone. High-resolution x-ray computed tomography in geosciences: A review of the current technology and applications. *Earth-Science Reviews*, 123:1-17, 2013, each incorporated herein by reference in their entirety. The digitized model is obtained by performing high resolution (i.e., micrometer and nanometer), three dimensional (3D), computed X-ray tomography (CT) scans of the core. The models obtained are analyzed and turned into realistic representations of the internal structure of the rock. Subsequently, numerical experiments are performed on the 3D models to determine the required properties. Since only virtual representations are used for testing purposes, the experiments can be performed repeatedly under different scenarios. DRP has been used to study reservoir rock mineralogy, elastic properties, flow and transport phenomena, etc. See A. Golab, M. A. Knackstedt, H. Averdunk, T. Senden, A. R. Butcher, and P. Jaime. 3d porosity and mineralogy characterization in tight gas sandstones. *The Leading Edge*, 29:1476-1483, 2010; M. Dernaika, Y. N. Uddin, S. Koronfol, O. Al Jallad, and G. Sinclair. Multiscale rock analysis for improved rock typing in complex carbonates. In *International Symposium of the Society of Core Analysts*, St. Johns Newfoundland and Labrador, Canada, 16-21 Aug. 2015, 2015; C. Arns, M. Knackstedt, W. Pinczewski, and E. Garboczi. Computation of linear elastic properties from microtomographic images: Methodology and agreement between theory and experiment. *Geophysics*, 67:1396-405, 2002; E. Saenger, F. Enzmann, Y. Keehm, and H. Steeb. Digital rock physics: effect of fluid viscosity on effective elastic properties. *Journal of Applied Geophysics*, 24:236-41, 2011; M. Blunt. Flow in porous media—pore-network models and multiphase flow. *Current Opinion in Colloid and Interface Science*, 6:197-207, 2001; C. Arns, M Knackstedt, M. Pinczewski, and W. Lindquist. Accurate estimation of transport properties from microtomographic images. *Geophysical Research Letters*, 28(17):3361-3644, 2001; Y. Keehm, T. Mukerji, and A. Nur. Permeability prediction from thin sections: 3d reconstruction and lattice-boltzmann ow simulation. *Geophysical Research Letters*, 31(4), 2004; S. Ovaysi and M. Piri. Direct pore-level modeling of incompressible fluid flow in porous media. *Journal of Computational Physics*, 229(19):7456-7476, 2010; and S. Aryana and A. R. Kovscek. Nonequilibrium effects and multiphase flow in porous media. *Transport in Porous Media*, 97:373-394, 2013, each incorporated herein by reference in their entirety.

Recently, permeability prediction has gained significant attention. For example, in at least one instance quantifying the permeability anisotropy in carbonates was attempted. In other instances, an inverse approach was adopted in which the measured porosity was used as a starting point to estimate the permeability, and multiscale microtomography was used to try and obtain a reasonable representation of the pore-network structure. Furthermore, other attempts have been made to quantify the effect of image resolution on simulated permeability. See H. Sun, S. Vega, and G. Tao. Analysis of heterogeneity and permeability anisotropy in carbonate rock samples using digital rock physics. *Journal of Petroleum Science and Engineering*, 156:419-429, 2017; E. H. Saenger, S. Vialle, M. Lebedev, D. Uribe, M. Osorno, M. Duda, and H. Steeb. Digital carbonate rock physics. *Solid Earth*, 7:1185-1197, 2016; M. S. Jouini, S. Vega, and A.

Al-Ratrout. Numerical estimation of carbonate rock properties using multiscale images. *Geophysical Prospecting*, 63(2):405-421, 2014; K. Rahimov, A. M. AlSumaiti, and M. S. Jouini. Quantitative analysis of absolute permeability and porosity in carbonate rocks using digital rock physics. In 22nd Formation Evaluation Symposium of Japan, 29-30 September, Chiba, Japan. Society of Petrophysicists and Well-Log Analysts, 2016. SPWLA-JFES-2016-J; H. Sun, S. Vega, and G. Tao. Determination of transport properties in carbonate rock sample using multi-scale ct images. In *78th EAGE Conference and Exhibition* 2016, 30 May-2 Jun., Vienna, Austria, 2016; F. D. E. Latief, Z. Fauzi, U. Irayani, and G. Dougherty. The effect of x-ray micro computed tomography image resolution on flow properties of porous rocks. *Journal of Microscopy*, 266(1):69-88, 2017; and Y. Bazaikin, B. Gurevich, S. Iglauer, T. Khachkova, D. Kolyukhin, M. Lebedev, V. Lisitsa, and G. Reshetova. Effect of ct image size and resolution on the accuracy of rock property estimates. *Journal of Geophysical Research: Solid Earth*, 122(5):3635-3647, 2017, each incorporated herein by reference in their entirety.

Due to the opaque nature of most porous media, permeability is usually obtained during experiments by measuring flow speed under a certain pressure gradient. With the development of imaging technologies, the interior pore structures within rock samples can be visualized. A void fraction, which is related to the porosity of the rock, can be characterized experimentally by mercury porosimetry. When a rock porosity is measured, the measured value can be used as a threshold value in the grayscale to differentiate pore sections from rock sections. The threshold value can be used in filtering the attenuation values of the X-ray microtomography image to generate a binary representation of the rock and the pore space, wherein 0 represents a rock site and 1 represents a pore site. See E. S. Boek and M. Venturoli. Lattice-boltzmann studies of fluid flow in porous media with realistic rock geometries. *Computers and Mathematics with Applications*, 59:2305-2314, 2010, incorporated herein by reference in its entirety. The binarization process defines all voxels with monochromatic values less than a threshold to be pore space or void, and the monochromatic values greater than a threshold to be solid such that the segmented porosity monotonously decreases with the threshold value. See A. Hosa, A. Curtis, and R. Wood. Calibrating lattice boltzmann flow simulations and estimating uncertainty in the permeability of complex porous media. *Advances in Water Resources*, 94:60-74, 2016, incorporated herein by reference in its entirety. By using computational methods, direct flow simulations through the pore space of rock samples can be used to calculate permeabilities. The Lattice-Boltzmann method (LBM) is one such method that can be used to calculate permeabilities. Simplicity and flexibility in dealing with complicated geometry are some of the advantages LBM has over conventional methods of computational fluid dynamics (CFD) such as the finite-volume method (FVM) in which the flow is simulated by solving the Navier-Stokes equations directly. See Y. H. Qian, D. dHumieres, and P. Lallemand. Lattice bgk models for navier-stokes equation. *Europhysics Letters*, 17:479-484, 1992; and H. Chen, S. Y. Chen, and W. H. Matthaeus. Recovery of the navier-stokes equations using a lattice-gas boltzmann method. *Physical Review A*, 45:5339-5342., 1992, each incorporated herein by reference in their entirety. Additionally, since LBM utilizes the nearest neighbor information in an explicit updating algorithm, the LBM is ideal for large scale parallel computations.

In view of the difficulties and drawbacks of the existing permeability methods, the present disclosure describes a method and/or system that may be used to determine the absolute permeability of reservoir carbonate rocks. To do so, the method of the present disclosure describes a method of comparing numerical estimates and experimental data obtained from digital rock physics and lattice-boltzmann methods to determine absolute permeability and thus, avoid upscaling computations.

SUMMARY OF THE INVENTION

The present disclosure describes a method that can determine absolute permeability in carbonate without the use of upscaling computations. In particular, the method of the present disclosure describes a selection procedure for subdomains such that the subdomain can be scanned at high resolution as a representative sample of the carbonate rock. By scanning an accurate representation of the carbonate rock as described in the present disclosure and performing permeability simulations, upscaling computations such as homogenization and volume averaging typically used in conventional permeability determining methods may be avoided.

As a first step of predicting the absolute permeability as described in the present disclosure, the permeability of at least three samples retrieved from a reservoir carbonate rock of a set of representative regions is experimentally determined using NMR analysis and MICP analysis, wherein each of the set of representative regions provides an accurate representation of the reservoir carbonate rock. More specifically, pore-body radius distribution is determined via NMR analysis and pore-throat size distribution is determined via the MICP analysis, so as to determine an experimental permeability.

Next, to identify regions with large porosity within each of the at least three samples, a series of low resolutions X-ray scans is performed. Subsequently, a series of high resolution X-ray scans is performed on selected regions positioned outside the large porosity regions within each of the at least three samples. Next, permeability simulation by numerical modelling of pore-scale flow is performed on each of the at least three samples to determine a computed permeability. The experimental permeability obtained from the NMR analysis and the MICP analysis is then compared with the computed permeability obtained from the permeability simulations to determine the absolute permeability.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
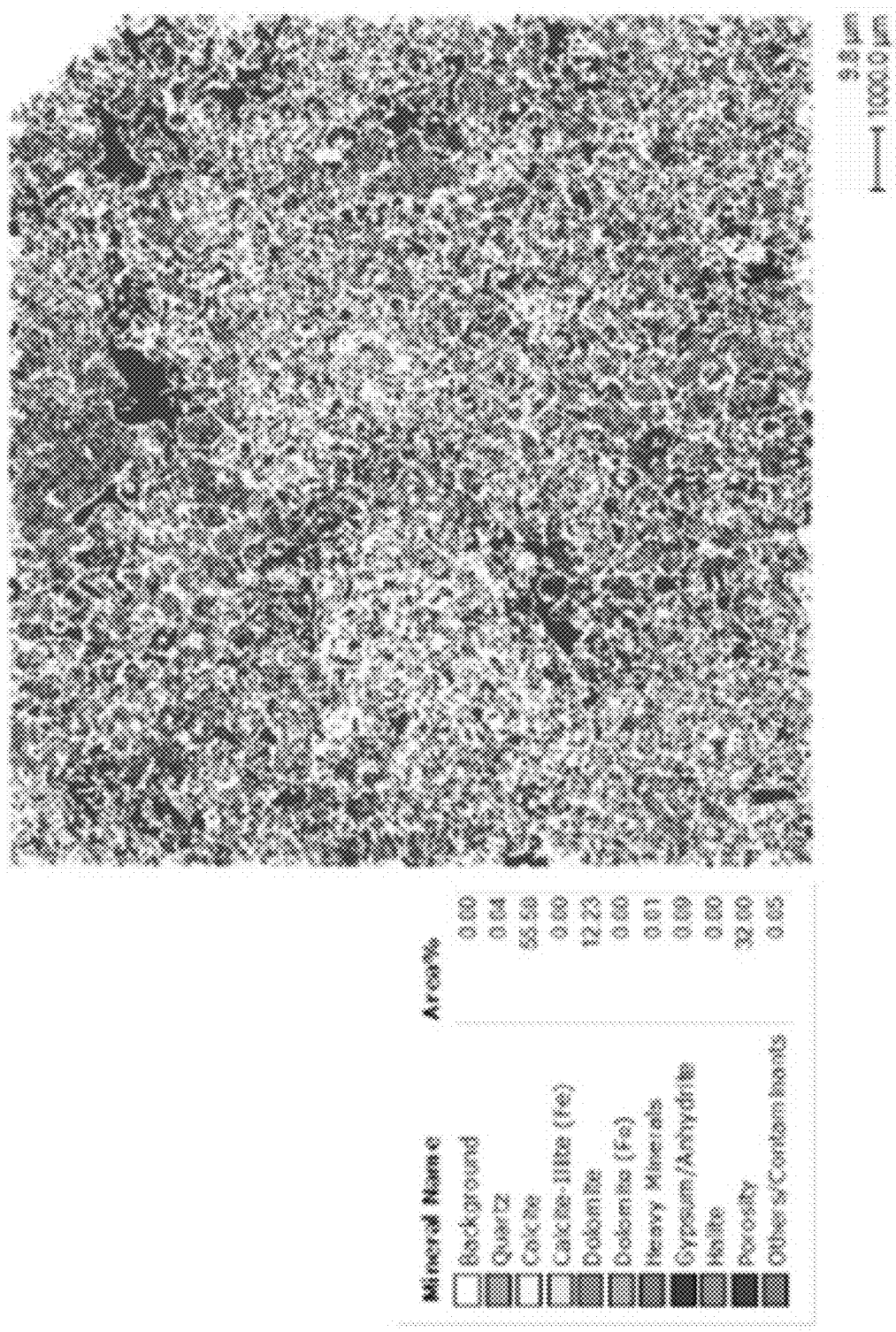
FIG. 1A is an analysis obtained for a mineral composition of a first sample from at least three core samples retrieved from a reservoir carbonate rock.

All illustrations of the drawings are for the purpose of describing selected embodiments of the present disclosure and are not intended to limit the scope of the present disclosure or accompanying claims.

The present disclosure describes a method for predicting absolute permeability of reservoir carbonate rocks. The process involves the comparison of experimental data and numerical estimates obtained via digital rock physics and Lattice-Boltzmann methods.

In a first step of determining absolute permeability, at least three core samples of a reservoir carbonate rock are analyzed to determine a first pore structure. Each of the at least three core samples will have varied porosity, pore-network structure, and modality. For example, the porosity of a first sample will be different from the porosity of a second sample and a third sample.

Several mechanisms appear particularly important in producing or changing porosity and pore-size distribution in carbonate rocks. Primary interparticle porosity is formed by deposition of well sorted calcareous sand or gravel under the influence of strong currents or waves or by local production of calcareous sand-size particles with sufficient rapidity to deposit particle on particle with little or no interstitial mud. Dissolution of interstitial mud in a calcareous sand can produce a micro-vuggy porosity resembling interparticle pore space. Simple cementation by calcite, anhydrite, dolomite, or quartz destroys porosity and pore size. Calcite cement appears to be especially common where the particles are monocrystalline, such as crinoid fragments. Primary constructional rugs are produced by formation of a rigid or semi-rigid framework. This framework may be organic or inorganic, and the inter framework pockets may be filled with sediment or later with cement.

The patchy growth of either scattered dolomite euhedral or masses of interlocking dolomite anhedral, followed or accompanied by dissolution of the nonreplaced limestone relict patches, produces vugs. A similar textural history of replacement by one mineral and dissolution of the nonreplaced patches is found in limestone replaced by fine networks of chert. Dissolution of the nonreplaced limestone produces porosity. Dolomitization of a limestone with interparticle or vuggy porosity without cementation of the earlier void space permits preservation of that void space.

When analyzing the at least three core samples to determine a first pore structure of the carbonate rock, a nuclear magnetic resonance (NMR) analysis is initially used to determine a pore-body radius distribution, and a mercury-injection capillary-pressure (MICP) analysis is subsequently used to determine a pore-throat radius distribution.

Nuclear Magnetic Resonance (NMR) spectroscopy is an analytical chemistry technique used in quality control and research for determining the content and purity of a sample as well as its molecular structure. For example, NMR can quantitatively analyze mixtures containing known compounds. For unknown compounds, NMR can either be used to match against spectral libraries or to infer the basic structure directly. Once the basic structure is known, NMR can be used to determine molecular conformation in solution as well as studying physical properties at the molecular level such as conformational exchange, phase changes, solubility, and diffusion. The principle behind NMR is that many nuclei have spin and all nuclei are electrically charged. If an external magnetic field is applied, an energy transfer is possible between the base energy to a higher energy level (generally a single energy gap). The energy transfer takes place at a wavelength that corresponds to radio frequencies and when the spin returns to its base level, energy is emitted at the same frequency. The signal that matches this transfer is measured in many ways and processed in order to yield an NMR spectrum for the nucleus concerned.

Resonant frequency, sample handling, deuterated solvents, shim and lock, acquisition of spectra, chemical shift, J-coupling, second order coupling, and magnetic inequivalence are some of the basic techniques that can be used in NMR analysis. In resonant frequency, when a sample is placed in a magnetic field, NMR active nuclei such as hydrogen-1 and carbon-13, absorb electromagnetic radiation at a frequency characteristic of the isotope. The resonant frequency, energy of the radiation absorbed, and the intensity of the signal are proportional to the strength of the magnetic field. For example, in a 21 Tesla magnetic field, hydrogen atoms (commonly referred to as protons) resonate between 800 MHz-1000 MHz. It is common to refer to a 21 T magnet as a 900 MHz magnet since hydrogen is the most common nucleus detected, however different nuclei will resonate at different frequencies at this field strength in proportion to their nuclear magnetic moments.

An NMR spectrometer typically contains a spinning sample-holder inside a very strong magnet, a radio-frequency emitter and a receiver with a probe (an antenna assembly) that goes inside the magnet to surround the sample, optionally gradient coils for diffusion measurements, and electronics to control the system. Spinning the sample is usually necessary to average out diffusional motion, however some experiments call for a stationary sample when solution movement is an important variable. For instance, measurements of diffusion constants (diffusion ordered spectroscopy or DOSY) are done using a stationary sample with spinning off, and flow cells can be used for online analysis of process flows.

Upon excitation of the sample with a radio frequency (60-1000 MHz) pulse, a nuclear magnetic resonance response—a free induction decay (FID)—is obtained which is a very weak signal, and requires sensitive radio receivers to pick up. A Fourier transform is carried out to extract the frequency-domain spectrum from the raw time-domain FID. A spectrum from a single FID has a low signal-to-noise ratio, but it improves readily with averaging of repeated acquisitions. Good hydrogen-1 NMR spectra can be acquired with 16 repeats, which takes only minutes. However, for elements heavier than hydrogen, the relaxation time is rather long, e.g. around 8 seconds for carbon-13. Thus, acquisition of quantitative heavy-element spectra can be time-consuming, taking tens of minutes to hours.

With the chemical shift technique, given that the location of different NMR signals is dependent on the external magnetic field strength and the reference frequency, the signals are usually reported relative to a reference signal.

J-coupling or scalar coupling (a special case of spin-spin coupling) is between NMR active nuclei, wherein the coupling arises from the interaction of different spin states through the chemical bonds of a molecule and results in the splitting of NMR signals. For a proton, the local magnetic field is slightly different depending on whether an adjacent nucleus points towards or against the spectrometer magnetic field, which gives rise to two signals per proton instead of one. These splitting patterns can be complex or simple and, likewise, can be straightforwardly interpretable or deceptive. The coupling provides detailed insight into the connectivity of atoms in a molecule.

In second order coupling, the coupling constant is small in comparison with the difference in NMR frequencies between the inequivalent spins. If the shift separation decreases (or the coupling strength increases), the multiplet intensity patterns are first distorted, and then become more complex and less easily analyzed (especially if more than two spins are involved). Intensification of some peaks in a multiplet is achieved at the expense of the remainder, which sometimes almost disappear in the background noise, although the integrated area under the peaks remains constant. In most high-field NMR, however, the distortions are usually modest and the characteristic distortions (roofing) can in fact help to identify related peaks.

Spins that are chemically equivalent but are not indistinguishable (based on their coupling relationships) are termed magnetically inequivalent. For example, the 4 hydrogen sites of 1,2-dichlorobenzene divide into two chemically equivalent pairs by symmetry, but an individual member of one of the pairs has different couplings to the spins making up the other pair. Magnetic inequivalence can lead to highly complex spectra which can only be analyzed by computational modeling. Such effects are more common in NMR spectra of aromatic and other non-flexible systems, while conformational averaging about C—C bonds in flexible molecules tends to equalize the couplings between protons on adjacent carbons, reducing problems with magnetic inequivalence.

In general, when MICP analysis is performed, a tarred sample is placed in the instrument chamber which is then evacuated and flooded with mercury. Since mercury does not wet most substances and will not spontaneously penetrate pores by capillary action, it must be forced into the pores by the application of external pressure. The required equilibrated pressure is inversely proportional to the size of the pores, only slight pressure being required to intrude mercury into large macropores, whereas much greater pressures are required to force mercury into small pores. Mercury porosimetry analysis is the progressive intrusion of mercury into a porous structure under stringently controlled pressures. From the pressure versus intrusion data, the instrument generates volume and size distributions using the Washburn equation which describes the capillary flow in a bundle of parallel cylindrical tubes and is extended to be used with porous materials.

Pressure on the mercury is incrementally increased forcing mercury through progressively smaller pore throats. By the end of the experiment (at approximately 55,000 pounds per square inch absolute (psia)-60,000 psia) pores accessible through throats as small as 30 angstrom (Å)-40 Å in diameter are intruded. The volume of mercury forced into the sample is equivalent to the volume of porosity accessed. In a preferred embodiment, a preset filling pressure within a range of 1.5 psi-2.0 psi or 1.8 psi-2.0 psi, with a preferable preset filling pressure of 1.6 psi is applied.

After the NMR analysis and the MICP analysis are completed, the method of the present disclosure digitizes the at least three core samples using a series of low resolution X-ray scans. In this respect tomograms obtained from the X-ray scans may be combined numerically, for example using PerGeos Software (ThermoFisher Scientific) which produces the 3D digital representations of the rock samples. By doing so, a second pore structure is extracted for each of the at least three core samples. For validation purposes, the second pore structure obtained from the series of low resolution X-ray scans is compared with the first pore structure obtained via the NMR analysis and the MICP analysis. Moreover, by comparing the pore-body radius distribution of the first pore structure and the second pore structure, a set of large porosity regions of each of the at least three core samples is identified. Large porosity refers to pore radius of 0.01 to 1 mm, preferably 0.1 to 0.5 mm.

The set of large porosity regions can be, but is not limited to, vugs and caverns. Vugs are formed when mineral crystals inside rocks are removed through the processes of dissolution or erosion, which leave voids inside the rock. Most vugs are filled with water that is saturated with minerals and flows through the rock. This mineralization of vugs occurs in stages. Fine crystals are always found in vugs, as the open space of the cavity enables the development of external crustal forms.

The voxel size is an important component of image quality. Voxel is the 3-D analog of a pixel. Voxel size is related to both the pixel size and slice thickness. Pixel size is dependent on both the field of view and the image matrix. The pixel size is equal to the field of view divided by the matrix size. The matrix size is typically 128×, 256× or 512×. Pixel size is typically between 0.5 and 1.5 mm. The smaller the pixel size, the greater the image spatial resolution.

Increased voxel size results in an increased signal-to-noise ratio. The trade-off for increased voxel size is decreased spatial resolution. Voxel size can be influenced by receiver coil characteristics. For examples, surface coils indirectly improve resolution by enabling a smaller voxel size for the same signal-to-noise ratio.

Voxel size can contribute to artifacts in magnetic resonance imaging (MRI). Many magnetic resonance artifacts are attributable to errors in the underlying spatial encoding of the radiofrequency signals arising from image voxels. Motion artefacts can occur in the phase-encoding direction because a specific tissue voxel may change location between acquisition cycles, leading to phase encoding errors. This manifests as a streak or ghost in the final image, and can be reduced with image gating and regional presaturation techniques. In a preferred embodiment, a voxel volume of the series of low resolution X-ray scans is within a range of 25 cubic micrometers ($\mu m^3$)-35 $\mu m^3$, 28 $\mu m^3$-32 $\mu m^3$, with a preferable voxel volume of 30 $\mu m^3$.

When the set of large porosity regions is identified by comparing the first pore structure and the second pore structure, the method of the present disclosure proceeds to identify a set of inspection regions that is outside the set of large porosity regions, wherein the set of inspection regions is semi-randomly selected. As a subsequent step, a series of high resolution X-ray scans is performed on the set of inspection regions. Preferably, the voxel size used in the series of high resolutions X-ray scans will be lesser than a dominant pore-throat size within the at least three core samples. Moreover, each of the set of inspection regions will have a site volume within a range that can be, but is not limited to, 0.6 millimeter$^3$ (mm$^3$)-1.2 mm$^3$, 0.8 mm$^3$-1.2 mm$^3$, with a preferable site volume of approximately 1 mm$^3$. When performing the series of high resolution X-ray scans is completed, numerical modelling is performed on a set of representative regions selected from the set of inspection regions of each of the at least three core samples such that a permeability of the reservoir carbonate rock can be determined. Low-resolution scans have a voxel volume of 15-100 $\mu m^3$, preferably 20-80 $\mu m^3$, 25-60 $\mu m^3$, 30-50 $\mu m^3$ or about 40 $\mu m^3$, especially preferably about 30 $\mu m^3$. High-resolution scans have a voxel volume of 0.01-10 $\mu m^3$, 0.05-5 $\mu m^3$, 0.1-2.5 $\mu m^3$, 0.5-2 $\mu m^3$ or about 1.5 $\mu m^3$. In particular, the set of representative regions is selected to be most resemblant to the reservoir carbonate rock. More specifically, the set of representative regions captures the porosity and dominant pore-throat size of the reservoir carbonate rock. A determination of similarity, e.g., which representative regions are most similar to the reservoir carbonate rock, can be made utilizing the relationship of equation (5) below.

Figure 1B:
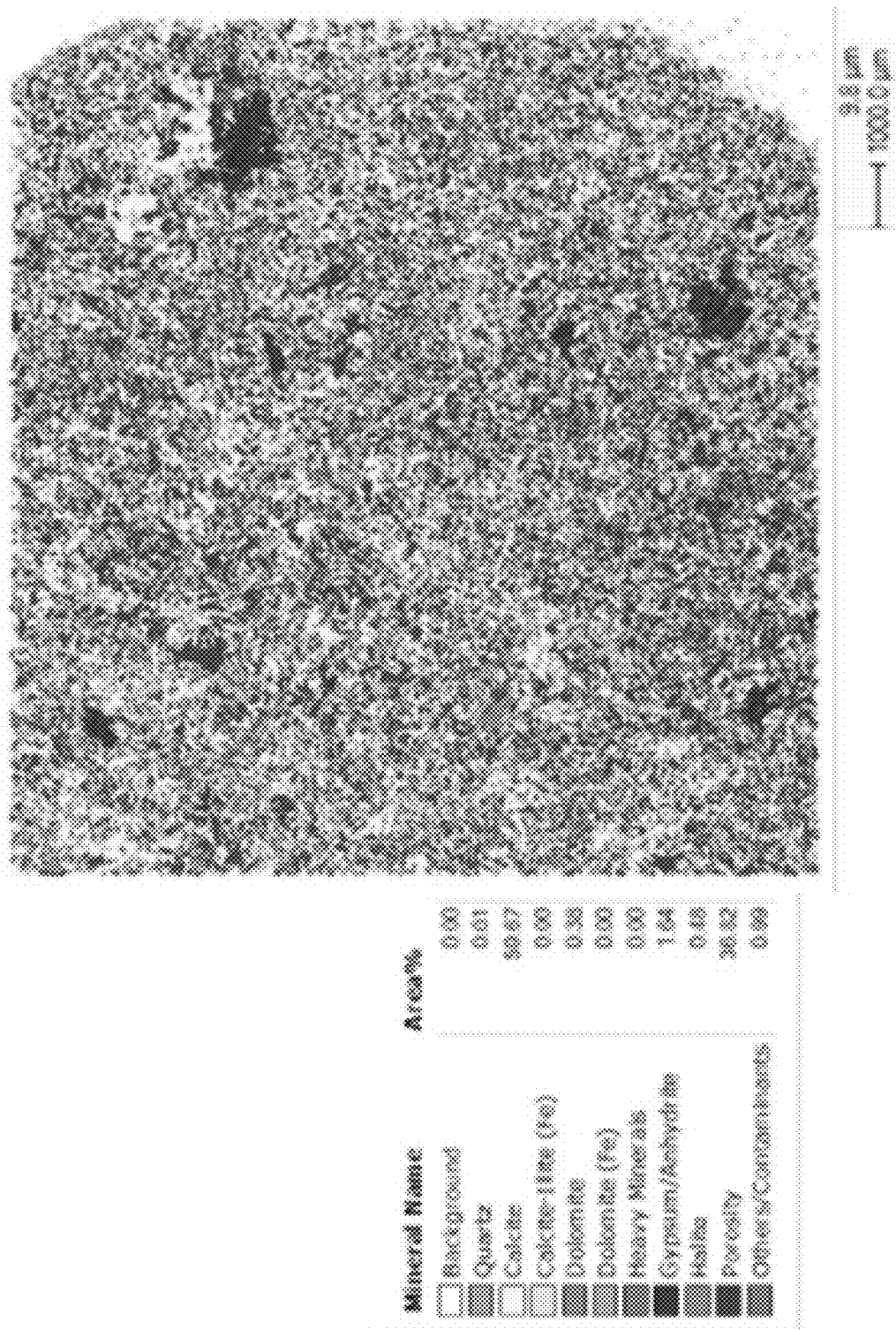
FIG. 1B is an analysis obtained for a mineral composition of a second sample from the at least three core samples retrieved from the reservoir carbonate rock.
Figure 1C:
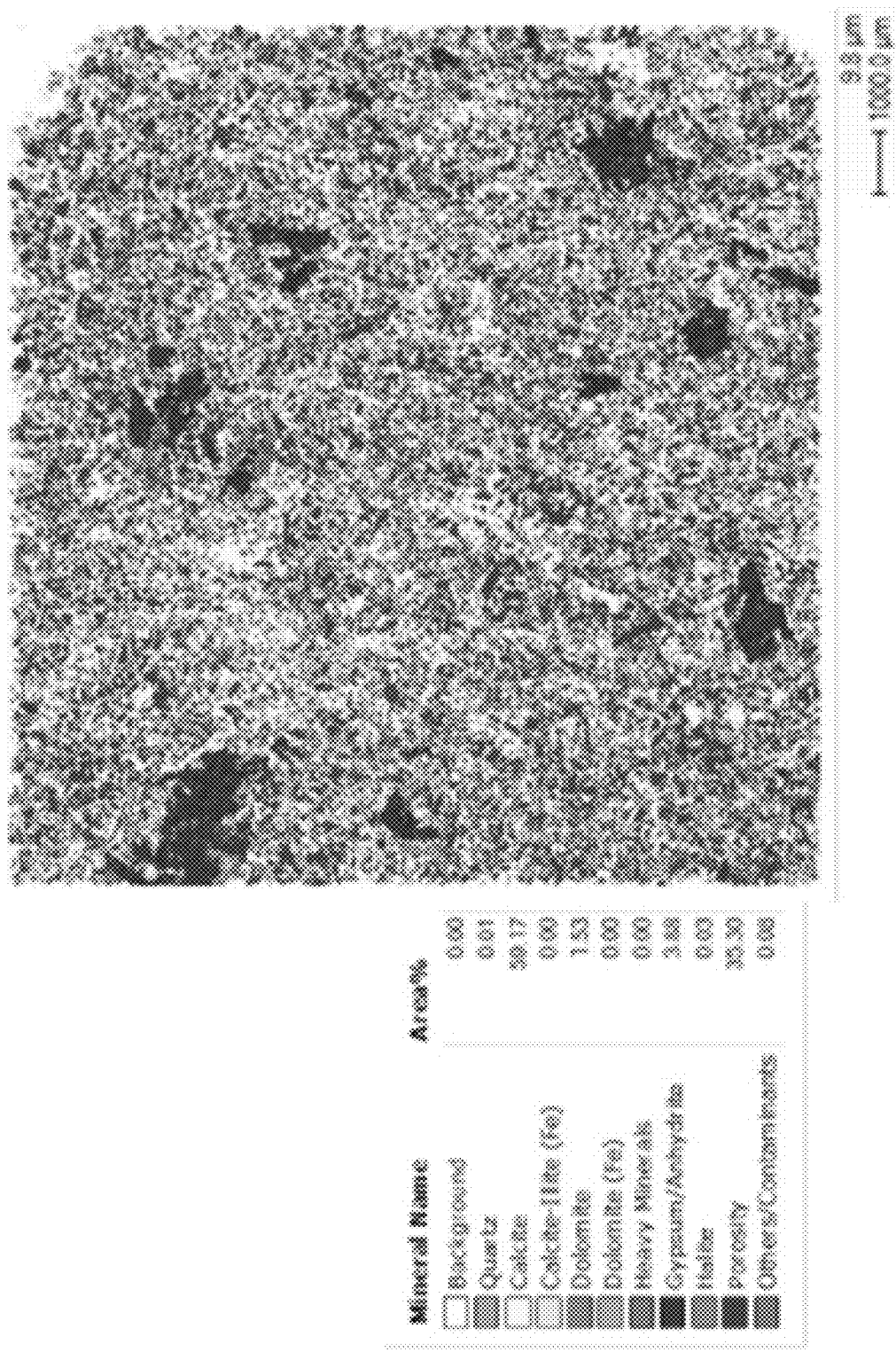
FIG. 1C is an analysis obtained for a mineral composition of a third sample from the at least three core samples retrieved from the reservoir carbonate rock.

In the example in consideration, the at least three samples were obtained from a reservoir carbonate rock in the Middle East. As described earlier, when the NMR analysis and the MICP analysis are performed on the at least three samples, a mineral composition is also simultaneously obtained. In a preferred embodiment, as seen in FIGS. 1A-1C, the mineral composition is obtained using quantitative evaluation of minerals by scanning electron microscopy (QEMSCAN) on a QEMSCAN 650F. QEMSCAN creates phase assemblage maps of a specimen surface scanned by a high-energy accelerated electron beam along a predefined raster scan pattern. Low-count energy-dispersive X-ray spectra (EDX) are generated and provide information on the elemental composition at each measurement point. The elemental composition in combination with back-scattered electron (BSE) brightness and x-ray count rate information is converted into mineral phases. QEMSCAN data includes bulk mineralogy and calculated chemical assays. By mapping the sample surface, textural properties and contextual information such as particle and mineral grain size and shape, mineral associations, mineral liberation, elemental deportment, porosity, and matrix density can be calculated, visualized, and reported numerically. Data processing capabilities include combining multiple phases into mineral groups, resolving mixed spectra (boundary phase processing), image-based filtering, and particle-based classification. Quantitative reports can be generated for any selected number of samples, individual particles, and for particle classes sharing similar compositional and/or textural attributes, such as size fractions or rock types. The mineral composition of each of the at least three samples are illustrated in FIGS. 1A-1C. Even though QEMSCAN is used in a preferred embodiment, other automated mineralogy analytical solutions that can be, but are not limited to, Mineral Liberation Analyzer (MLA) from FEI Company, Mineralogic from Zeiss, INCAMineral from Oxford Instruments, the TIMA (Tescan integrated mineral analyzer) from TESCAN and AMICS from Bruker may be used in other embodiments of the present disclosure.

In order to perform the NMR analysis on the at least three samples, a corresponding end trim is removed from each of the at least three samples, and the NMR analysis is performed on the corresponding end trim of each of the at least three samples to determine a NMR porosity. The NMR porosity does not depend on the mineralogy of the rock matrix, except in cases in which the formation contains significant amounts of ferromagnetic or paramagnetic materials. Hence, it is considered a lithology-independent measurement for most cases. Moreover, NMR porosity is not sensitive to either borehole or mudcake and does not require corrections because the measurement zone (i.e., sensitive volume) is focused within the formation, beyond the borehole wall and these influences. However, the rugosity of the wellbore will have to stay less than the range of DOI (depth of investigation of the tool) to keep the sensitive volume of measurement in the formation. The frequency of the NMR experiments, bottomhole temperature and the conductivity of the borehole fluid are the main controls of the DOI for the NMR tool as a function of its hardware specifics.

The series of low resolution X-ray scans, which is used to compare the first pore structure with the second pore structure, is also performed on the corresponding end trims removed from each of the at least three samples. The corresponding end trims of each of the at least three samples is cylindrical in a preferred embodiment of the present disclosure. Preferably, each of the corresponding end trims will have a diameter within a range of 20 mm-30 mm and a length within a range of 5 mm-10 mm.

After the corresponding end trim is removed from each of the at least three samples, a remainder of each of the at least three samples is used for MICP analysis. Helium porosity, $\varphi_{exp}$, and helium permeability, $\kappa_{exp}$, were measured from the remainder of each of the at least three samples. The NMR porosity, the helium porosity, and the helium permeability are used to determine an experimental permeability for the reservoir carbonate rock.

Total porosity is defined as the fraction of the bulk rock volume V that is not occupied by solid matter, and can be expressed either as a fraction or as a percentage. Porosity does not give any information concerning pore sizes, their distribution, and their degree of connectivity. Thus, rocks of the same porosity can have widely different physical properties. Different gases can be used in the process of measuring porosity. However, Helium is preferably used due to the small size of the helium molecule that can penetrate the smallest pores. Permeability represents the capacity of rocks to transmit fluids. Helium permeability is based on flow of helium through the sample caused by a pressure gradient allowing for an easy and efficient determination of gas permeability coefficients by using Darcy's law for compressible fluids. The hydraulic conductivities of the samples can be calculated from their measured permeabilities.

The permeability of the corresponding end trim is assumed to be consistent with the permeability of each of the at least three samples. The experimental data for the NMR porosity, $\varphi_{NMR}$, the Helium porosity, $\varphi_{exp}$, and helium permeability, $\kappa_{exp}$, and the MICP dominant pore-throat radius, $r_{MICP}$ are shown in table 1.

| Sample | Grain Density (g/cm$^3$) | $\varphi_{exp}$ (%) | $\varphi_{NMR}$ (%) | $\kappa_{exp}$ (mD) | $r_{MICP}$ (µm) |
|---|---|---|---|---|---|
| 1 | 2.730 | 24.7 | 18.6 | 54.5 | 1.61, 6.91 |
| 2 | 2.715 | 30.0 | 22.8 | 123.3 | 6.26 |
| 3 | 2.707 | 29.7 | 23.3 | 229.5 | 8.41 |

During the NMR analysis, the T2 relaxation experiments were performed as a bench-top, rock-core analyzer (Geo-Spec2-75, Oxford Instruments, UK). However, in other embodiments of the present disclosure, a Corona NMR Rock and Soil Core Analyzer, a source rock analyzer (SRA), or portable X-ray fluorescence analyzers may be used. In general, T2 relaxation refers to the progressive dephasing of spinning dipoles following the 90° pulse as seen in a spin-echo sequence due to tissue-particular characteristics, primarily those that affect the rate of movement of protons, most of which are found in water molecules. T2 relaxation is alternatively known as spin-spin relaxation.

In a preferred embodiment, the T2 relaxation experiments were conducted at a fixed field strength with a resonating frequency within a range of 1.5 megahertz (MHz)-2.5 MHz, with a preferable frequency range within a range of 2.0 MHz-2.5 MHz. The corresponding end trim from each of the at least three samples is saturated with deionized water for 24 hours at a pressure ranging from 1250 pounds per square inch (psi)-1750 psi, with a preferable pressure of 1500 psi. To obtain T2 relaxation decay curves using the echo time (TE) value constant at TE=0.053 milliseconds (ms), the standard Carr-Purcell-Meiboom-Gill (CPMG) pulse sequence is applied, wherein CPMG is a pulse sequence which is applied during nuclear magnetic resonance spectroscopy to measure spin-spin (T2) relaxation times. In a preferred embodiment of the present disclosure, an anticipated $T2_{max}$ was set to 2000 ms and the signal-to-noise ratio (SNR) for each experiment was retained at 50. However, in other embodiments of the present disclosure, the anticipated $T2_{max}$ and the SNR can be different.

As described earlier, the remainder of each of the at least three samples is used in the MICP analysis. In a preferred embodiment, a Micromeritics AutoPore IV 9520 Mercury Porosimeter is used for the MICP analysis. However in other embodiments, AutoPore V 9620 Mercury Porosimeter, poremaster 33 by quantachrome instruments or any other comparable instrument may be used. Prior to conducting the MICP analysis, the remainder of each of the at least three samples is dried, weighed, evacuated, and then immersed in mercury at a preset filling pressure within a range of 1.5 psi-2.0 psi, with a preferable preset filling pressure of 1.6 psi. During MICP analysis, approximately 100 preset pressure steps on a log-based scale are programmed and computer driven over the intrusion pressure range, which is within 1.6 psi-60,000 psi in a preferred embodiment. As a result, equally spaced, incremental mercury intrusion data points are obtained when pore aperture size distribution data is plotted on a semi-log graph. The dominant pore-throat radius corresponds to the peak of the curve.

As described earlier, the series of low resolution X-ray scans and the series of high resolution X-ray scans are used with the at least three samples. In a preferred embodiment, the series of low resolution X-ray scans has a pixel size within a range of 15 micrometers (µm)-20 µm. In a preferred embodiment, a Versa XRM-500 X-ray micro-CT scanner is used to scan the corresponding end trim of each of the at least three samples. However, other comparable scanners such as the ZEISS Xradia 520 Versa and the ZEISS Xradia 410 Versa scanners may be used in other embodiments of the present disclosure. The micro-CT technique may provide high resolution images of successively disturbed specimens. This, in turn provides an important basis to calculate the evolution of rock micro- and macro-scale properties using advanced numerical techniques at the pore scale. In addition, micro-CT is a useful method to study pore scale reactive displacement mechanisms and their effects on the evolution of rock properties. As described earlier, the first pore structure obtained from the NMR analysis is compared with the second pore structure obtained from digitizing the at least three samples with the series of low resolution X-ray scans.

When the dominant pore throat radius, $r_{MICP}$, is determined from the MICP analysis, the set of inspection regions outside the set of large porosity regions is identified in order to perform the series of high resolution X-ray scans. Next, the series high resolution X-ray scans is performed on approximately 2 selected regions from the set of inspection regions, wherein the 2 selected regions are the set of representative regions described earlier in a preferred embodiment. Even though two regions were selected to be set of representative regions in a preferred embodiment, in another embodiment three or more regions may be selected to be within the set of representative regions. Each of the set of representative regions will have a diameter within a range of 0.5 mm-1.5 mm, with a preferable diameter of 1 mm. The post selected sites are preferably cubic and have a dimension of 1 mm on each side. Numerical modelling and permeability simulations are performed on the set of representative regions such that the fluid flow direction of the simulations is consistent with the direction in which permeability is measured. In a preferred embodiment, the set of representative regions includes 2 sites of each of the at least three core samples. In comparison to conventional permeability determining methods, the use of 2 sites is manageable and non-destructive. Thus, the need to perform upscaling calculations representative of the entire sample is prevented.

When conducting the permeability simulations in the present disclosure, a single relaxation time LBM is used in the pore scale simulations of single phase single component flows to compute absolute permeabilities. The fundamental idea of the LBM is to construct a kinetic model simplified from the Boltzmann equation at mesoscale that incorporates the essential physical processes such that the macroscopic quantities satisfy the desired macroscopic governing equation, which is the navier-stokes equation. The nonslip boundary condition is imposed by using the simplest bounce back boundary condition, which is robust and efficient in problems with complicated geometry. Any numerical errors that occur will be in the same order of magnitude as those inevitably associated with the segmentation of the digital rock.

In the LBM simulations, the grids or lattices are uniformly distributed inside the computational domain and all computational quantities are defined at those discrete points. Generally, $\Delta x$ and $\Delta t$ denote the lattice distance and time step, respectively. At each point, several fixed lattice velocities, $e_\alpha$, which are either static with $\alpha=0$ or connect a current lattice at x to neighboring lattices at $x+\Delta t e_\alpha$, where $\alpha$ varies from 1 to Q−1 where Q is the total number of velocities. The magnitude of $e_\alpha$ depends on a ratio denoted by c wherein $c=\Delta x/\Delta t$. The 3-dimensional, 19-velocity (D3Q19) model is used in our three-dimensional simulations to determine $e_\alpha$ and the weighting factor $\omega_\alpha$. See Y. H. Qian, D. dHumieres, and P. Lallemand. Lattice bgk models for navier-stokes equation. Europhysics Letters, 17:479-484, 1992, incorporated herein by reference in its entirety. The explicit evolution algorithm of the density distribution function $f_\alpha(x, t)$ can be represented as:

$$F_\alpha(x+\Delta t e_\alpha, t+\Delta t) = f_\alpha(x,t) + \frac{f_\alpha^{eq}(x,t) - f_\alpha(x,t)}{\tau}, \quad (1)$$

where $\tau=3v\,\Delta t\,\Delta x^{-2}+0.5$ is determined by the kinematic viscosity v and the equilibrium distribution function is defined by:

$$f_\alpha^{eq}(x,t) = \rho\omega_\alpha\left[1 + \frac{3}{c^2}e_\alpha \cdot u^{eq} + \frac{9}{2c^4}(e_\alpha \cdot u^{eq})^2 - \frac{3}{2c^2}u^{eq}\cdot u^{eq}\right], \quad (2)$$

where $$\rho = \sum_{\alpha=0}^{Q-1} f_\alpha;$$

$$u^{eq} = \text{flow velocity} = u = \frac{1}{\rho}\sum_{\alpha=0}^{Q-1} e_\alpha f_\alpha$$

The transient pressure at each lattice is calculated as $p=c^2\rho/3$. Moreover, kinematic viscosity is defined as the measure of the inherent resistance of a fluid to flow when no external force is exerted, except gravity. Kinematic viscosity is the ratio of the dynamic viscosity to its density, a force independent quantity. Kinematic viscosity can be obtained by dividing the absolute viscosity of a fluid with the fluid mass density.

After convergence, the volumetric average velocity $\langle u \rangle_\Omega$ is used to compute three components of the permeability tensor $\bar{\kappa}$ as follows when the flow is driven in the y direction for example:

$$\kappa_{iy} = \frac{\mu L_y}{p_{in} - p_{out}}\langle u \rangle_\Omega \cdot e_i \quad (3)$$

$$= \frac{\mu L_y}{p_{in} - p_{out}}\frac{1}{N_{total}}\sum_{j\in void} u_j \cdot e_i; i = x, y, z$$

Where;
$L_y$—the size of computational domain along the y axis;
$\mu$—the dynamic viscosity;
$p_{in}-p_{out}$—the pressure difference between inlet and outlet;
$u_j$—velocity of the void grid j;
$N_{total}$—total lattice number;
$e_i$—unit vector along the i-th axis;
In the permeability simulations conducted in the present disclosure, flow direction is driven by a pressure difference that exists between the inlet and the outlet. Therefore, only the permeability component, which is denoted by $\kappa$, is considered along the flow direction.

When considering convergence, in the single-phase, single-component simulations using the ordinary LBM, the number of time steps required to reach steady state mostly depends on the lattice (or voxel) number. In particular, the number of time steps along the driven direction also depends on the tortuosity of the rock geometry (namely rock-dependent) and dimensionless relaxation time $\tau$. Tortuosity underpins the rigorous relationships between transport processes in rocks, and ties them with the underlying geometry and topology of their pore spaces. Tortuosity can be redefined in terms of the energetic efficiency of a flow process. The efficiency is related to the rate of entropy dissipation (or isothermally, energy dissipation) with respect to a simple, non-tortuous model medium using the postulates of non-equilibrium thermodynamics. In particular, tortuosity is an intrinsic property of a porous material usually defined as the ratio of actual flow path length to the straight distance between the ends of the flow path. The number of time steps is certainly independent of $\Delta x$ (e.g., voxel size as in the current study), $\Delta t$ and the pressures used initially and at the boundaries.

In general, a LBM simulation is considered to be converged when the relative change over a certain number of time steps (e.g., 1000 time steps) is smaller than a preset tolerance (e.g., $10^{-5}$). However, based upon the rock samples as well as the convergence criteria that is been implemented, different convergence speeds and computational times may be achieved. In one example, 5000 to 8000 time steps were used for the simulations of both $128^3$ lattices and $512^3$ lattices with $\tau=0.6$. See E. S. Boek and M. Venturoli. Lattice-boltzmann studies of fluid flow in porous media with realistic rock geometries. *Computers and Mathematics with Applications*, 59:2305-2314, 2010, incorporated herein by reference in its entirety.

In another example, simulations for $128^3$ lattices and $512^3$ lattices were performed wherein more than 25,000 time steps were used to achieve equilibration. See M. C. Sukop, H. B. Huang, C. L. Lin, M. D. Deo, K. Oh, and J. D. Miller. Distribution of multiphase fluids in porous media: comparison between lattice Boltzmann modeling and micro-x-ray tomography. *Physical Review E*, 77:026710, 2008, incorporated herein by reference in its entirety. In another example, simulations for $100^3$ lattices were performed wherein 100,000 time steps were used to achieve convergence. See A. Hosa, A. Curtis, and R. Wood. Calibrating Lattice Boltzmann flow simulations and estimating uncertainty in the permeability of complex porous media. *Advances in Water Resources*, 94:60-74, 2016, incorporated herein by reference in its entirety.

In a different instance, when the convergence study was conducted for both sandstone and tight-sandstone samples using $\tau=1$, the simulation of the sandstone sample with 160*160*30 voxels took 35,000 time steps to converge. On the other hand, the simulation of the tight-sandstone with 200*200*50 voxels took 162,000 time steps to converge. See R. R. Li, Y. S. Yang, J. X. Pan, G. G. Pereira, J. A. Taylor, B. Clennell, and C. N. Zou. Lattice boltzmann modeling of permeability in porous materials with partially percolating voxels. *Physical Review E*, 90:033301, 2014, incorporated herein by reference in its entirety.

Figure 2A:
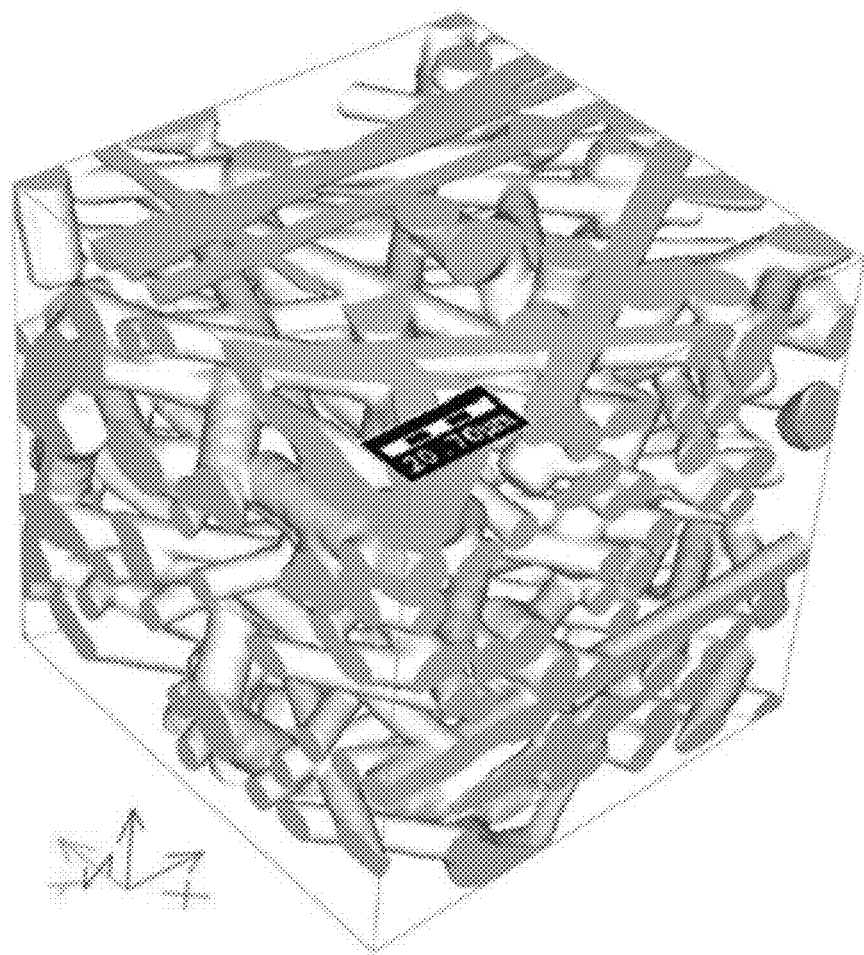
FIG. 2A is a Lattice-Boltzmann Method (LBM) simulation of a fiber geometry with $100^3$ voxels.
Figure 2B:
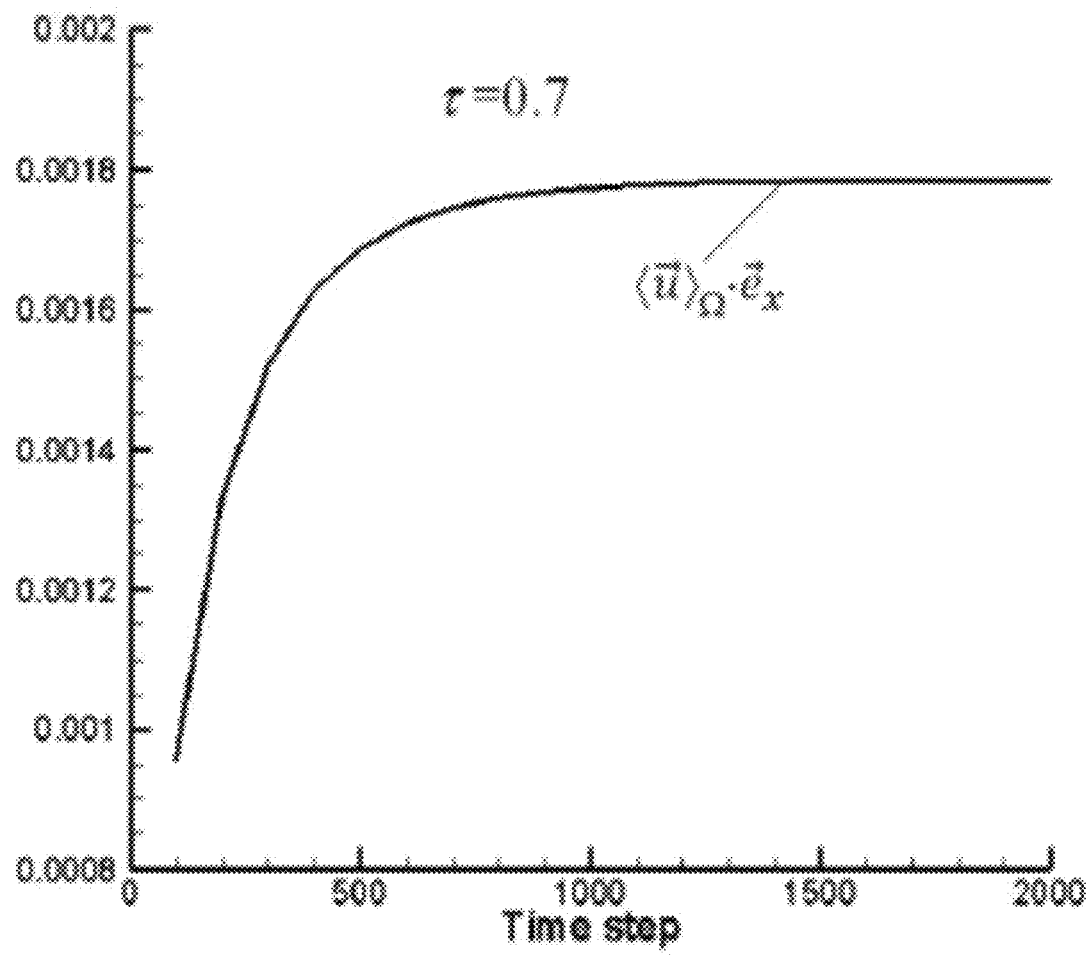
FIG. 2B is a graph illustrating the convergence processes of volumetric velocities at dimensionless relaxation time τ=0.7.
Figure 2C:
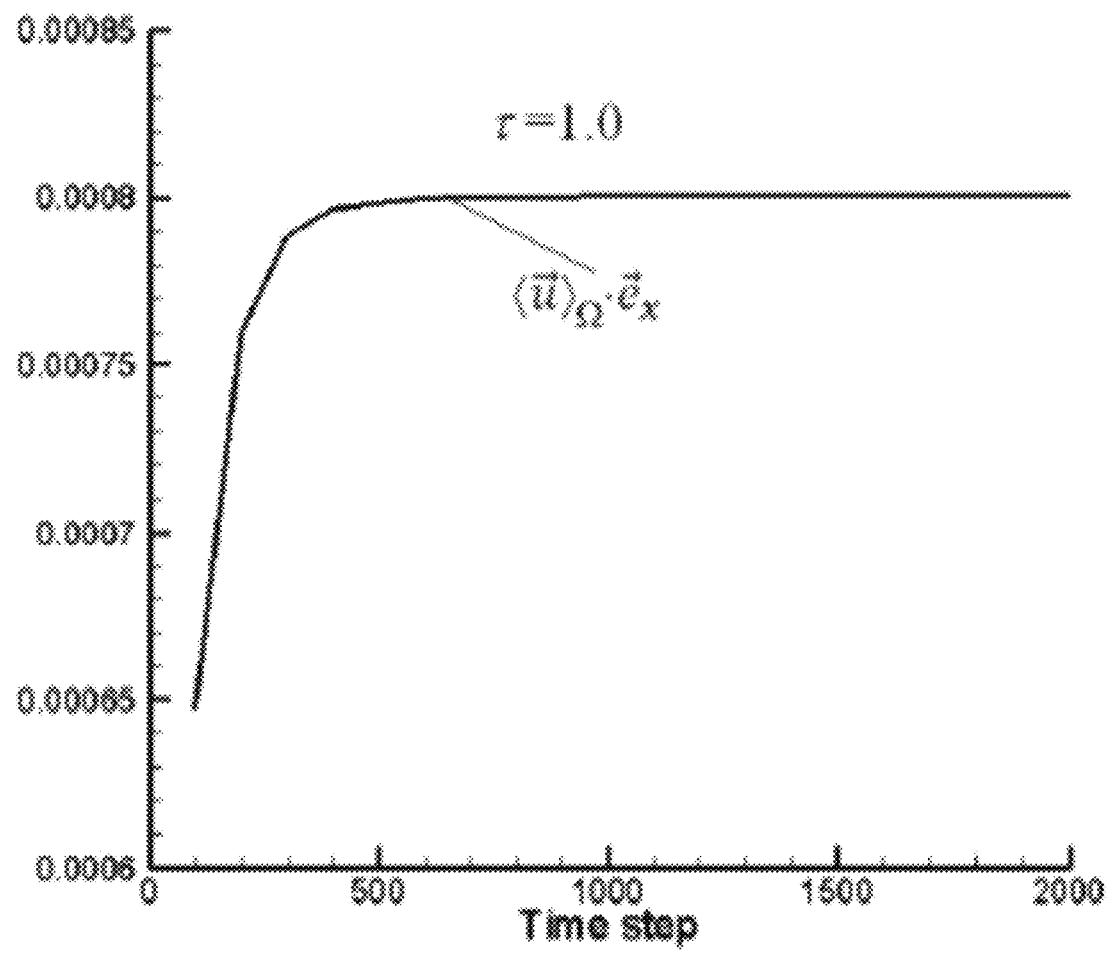
FIG. 2C is a graph illustrating the convergence processes of volumetric velocities at dimensionless relaxation time τ=1.0.

To analyze the variation of convergence speed when simulating different rock samples, the influence of relaxation time $\tau$ on the convergence speed in the simulation is considered. In this instance, a lattice fiber geometry with $100^3$ voxels, where the porosity is high and the tortuosity is low is considered. As seen in FIGS. 2A-2C, when $\tau=0.7$ approximately 1500 time steps are required for convergence.

On the other hand, when τ=1.0, approximately 700 time steps are required for convergence. Thus, the relationship between convergence speed and relaxation time is seen. In a preferred embodiment, τ=0.7 is used for experimentation purposes to reduce undesired slippage effect, wherein slippage is the phenomenon in which natural gas from a reservoir bypasses crude oil and water (basically liquids) that is released from the capillary openings of porous oil reservoir formations and approaches to the mean free path of the natural gas. In other terms, slippage can also be defined as the gas movement through liquid phase of the reservoir front. This phenomenon also helps the liquid to move forward to the low pressure zones (i.e., toward the earth's surface). The use of τ=0.7 can increase central processing unit (CPU) time when compared to higher values of τ. Lower τ values converges to higher volumetric average velocities since the kinematic viscosity decreases with τ.

Figure 3A:
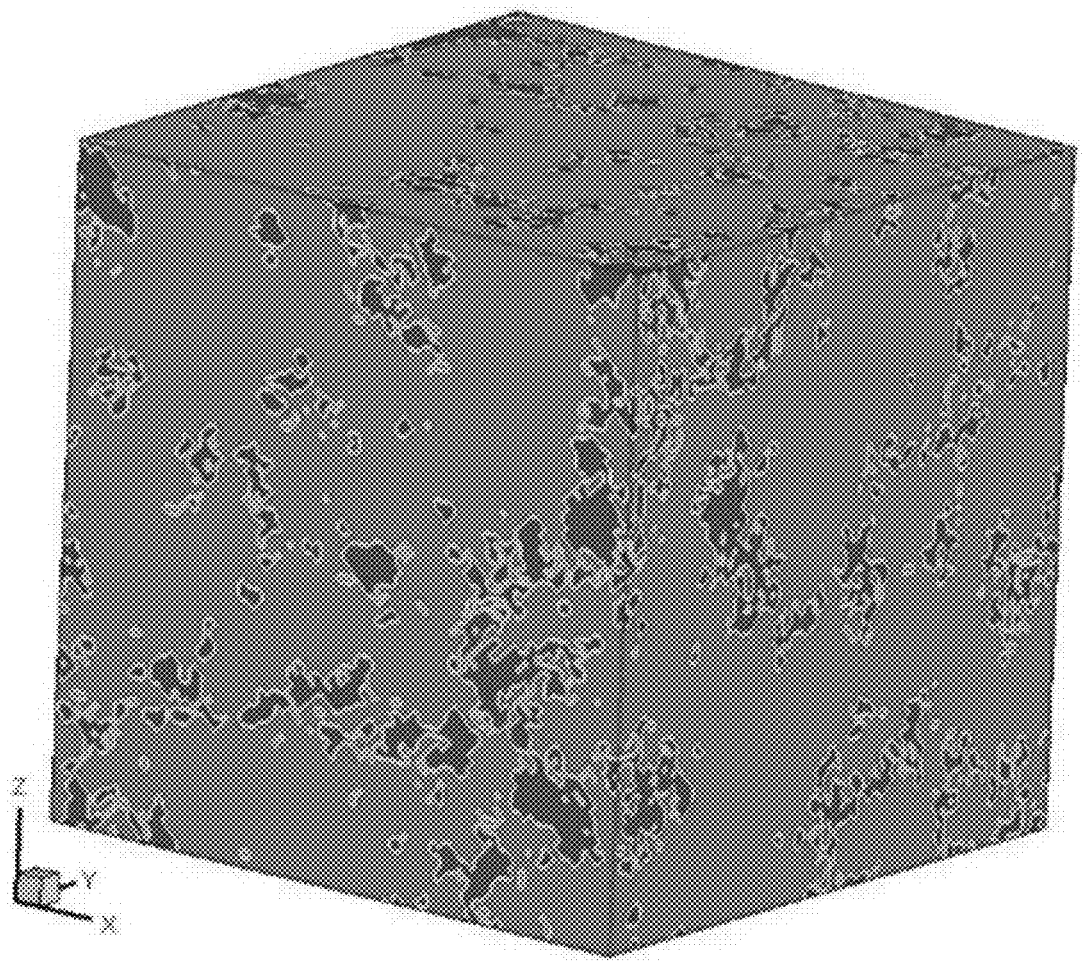
FIG. 3A is a LBM simulation of the original rock geometry, wherein the overall porosity is low.
Figure 3B:
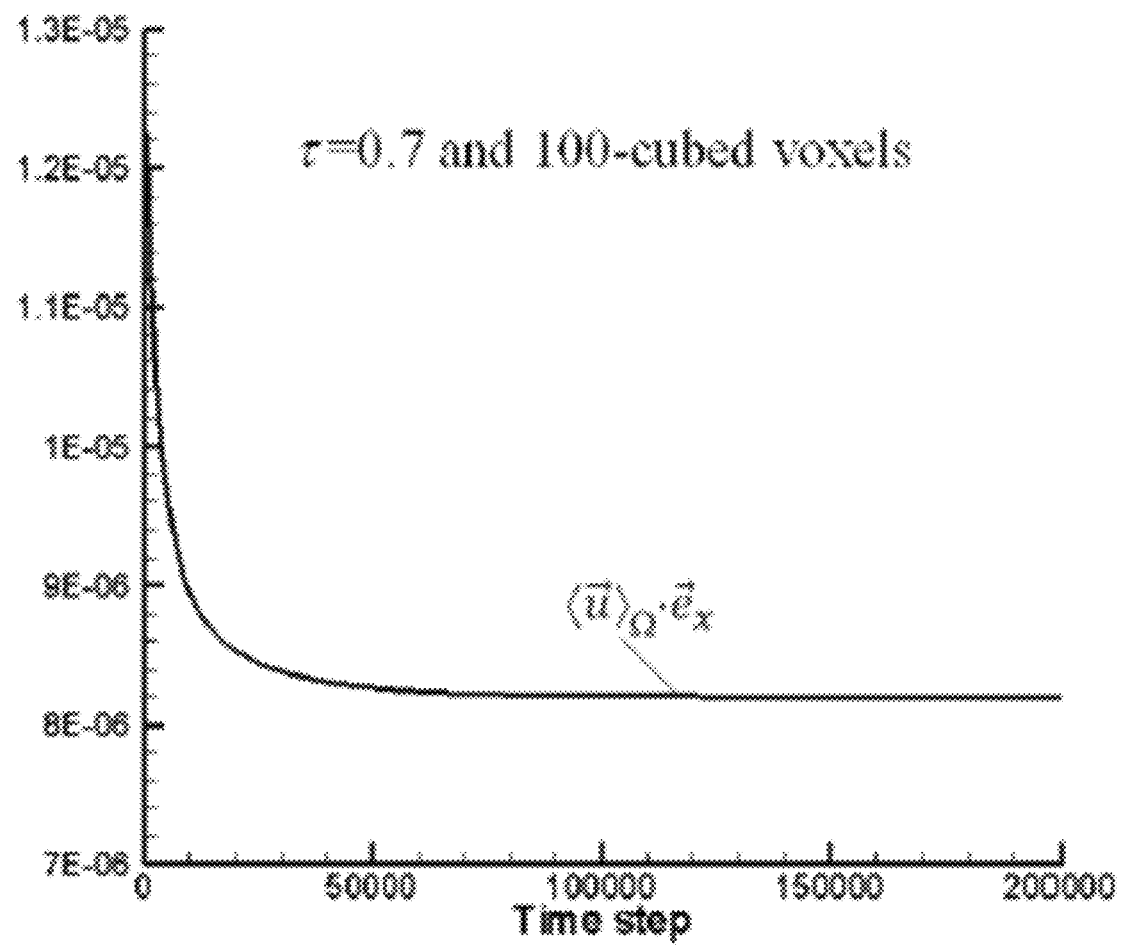
FIG. 3B is a graph illustrating the convergence processes of volumetric velocities at τ=0.7 and original rock geometry with $100^3$ voxels.
Figure 3C:
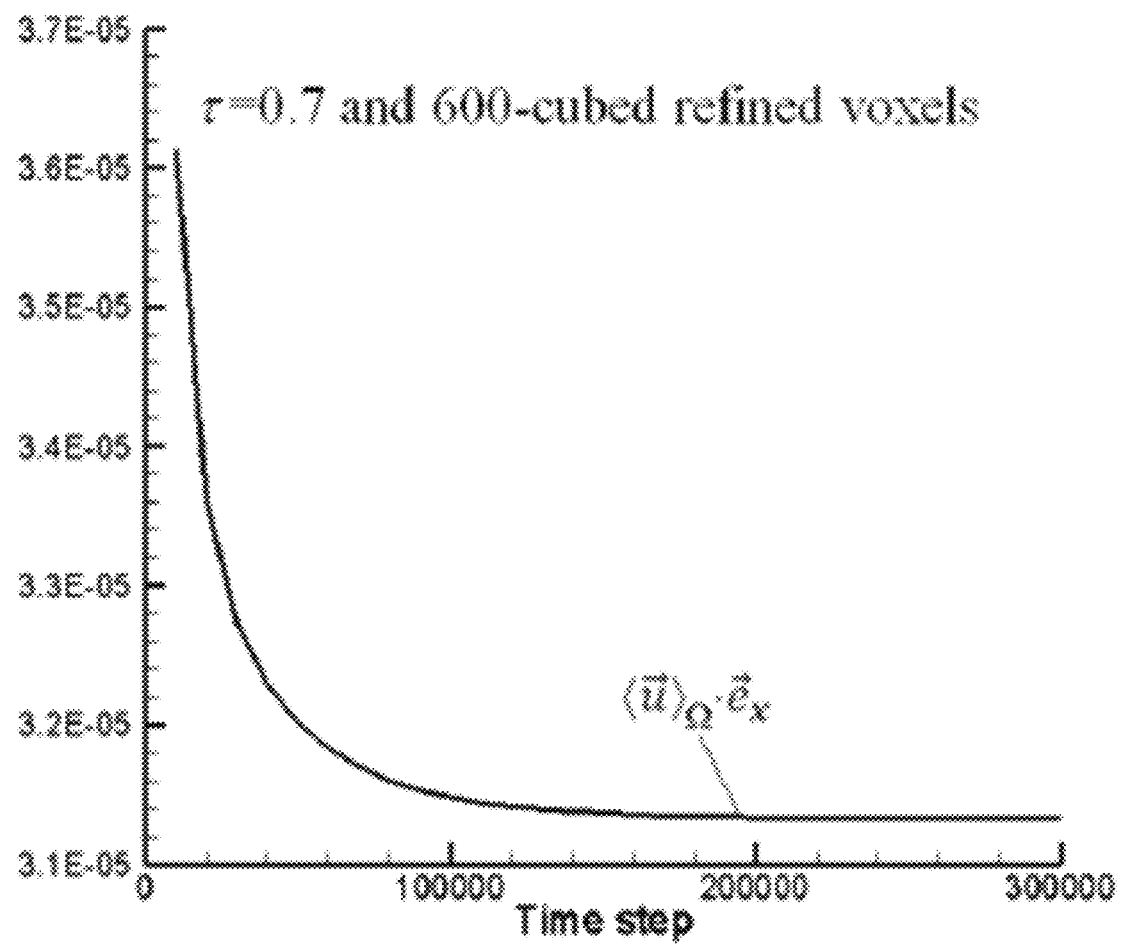
FIG. 3C is a graph illustrating the convergence processes of volumetric velocities at τ=0.7 and original rock geometry with $600^3$ voxels.

In order to determine the dependence of convergence speed on the tortuosity of a rock geometry, simulations were conducted on a rock geometry with a low porosity (φ=0.1647) and $100^3$ voxels at τ=0.7. As illustrated in FIGS. 3A-3C, with a low porosity value and τ=0.7, approximately 120,000 time steps were required for convergence. In comparison, with a high porosity value and τ=0.7, approximately 1,500 time steps were required. Thus, the dependence of the convergence speed on tortuosity is clear. However, the dependence should not be interpreted as a porosity dependent phenomenon since porosity can exist in separate passages, and the porosity can be independent of the number of passages that give the porosity value.

When the simulation was conducted at τ=0.7 for a rock geometry of $600^3$ voxels, to study the dependence of the convergence speed on the lattice number, the number of time steps to convergence increased to approximately 200,000 although the tortuosity and the τ remained unchanged.

The two simulations, with the $100^3$ voxel geometry and the $600^3$ voxel geometry, converge to different volumetric average velocities due to different kinematic viscosities and Knudsen numbers (Kn). When $100^3$ voxels were used, the computed permeability was within a range of 12.99 nano Darcy (nD)-13.10 nD. On the other hand, when $600^3$ voxels were used, the computed permeability was within a range of 8.200 nD-8.4 nD. The differences in permeability values is mainly due to different Kn numbers that decrease with increasing voxel numbers inside a pore space. More specifically, Kn is a dimensionless number defined as the ratio of the molecular mean free path length to a representative physical length scale. This length scale could be, for example, the radius of a body in a fluid. The Knudsen number helps determine whether statistical mechanics or the continuum mechanics formulation of fluid dynamics should be used to model a situation.

Statistical mechanics shows how the concepts from macroscopic observations (such as temperature and pressure) are related to the description of microscopic state that fluctuates around an average state. It connects thermodynamic quantities (such as heat capacity) to microscopic behavior, whereas, in classical thermodynamics, the only available option would be to measure and tabulate such quantities for various materials.

Continuum mechanics deals with physical properties of solids and fluids which are independent of any particular coordinate system in which they are observed. These physical properties are then represented by tensors, which are mathematical objects that have the required property of being independent of coordinate system. These tensors can be expressed in coordinate systems for computational convenience.

If the Knudsen number is near or greater than one, the mean free path of a molecule is comparable to a length scale of the problem, and the continuum assumption of fluid mechanics is no longer a good approximation. In such cases, statistical methods should be used.

As described earlier, the computed permeability depends on the selection of τ in the ordinary LBM simulations using the BGK model. In particular, the computed permeability depends on the Klinkenberg slippage effect where the Kn number is not close to zero as clearly elucidated in Li et al (2016). See B. Ferreol and D. H. Rothman. Lattice-boltzmann simulations of flow through fontainebleau sandstone. *Transport in Porous Media,* 20:3-20, 1995; Hosa et al. (2016); Boek et al. (2010); C. Pan, L. S. Luo, and C. T. Miller. An evaluation of lattice boltzmann schemes for porous medium flow simulation. *Computer & Fluids,* 35:898-909, 2006; P. Prestininzi, A. Montessori, M. L. Rocca, and S. Succi. Reassessing the single relaxation time lattice boltzmann method for the simulation of darcys flows. *International Journal of Modern Physics C,* 27:1650037, 2016; and J. Li, M. T. Ho, and Y. H. Wu, L. and Zhang. Lattice boltzmann modeling of intrinsic permeability, arxiv: 1609.09685 [physics.flu-dyn]. arXiv:1609.09685, 2016, each incorporated herein by reference in their entirety. With a higher Kn number, the ratio between the computed permeability and the intrinsic permeability will be higher. In ordinary LBM simulations, with a 2-dimensional, 9-velocity (D2Q9) model or a D3Q19 model, Kn can be expressed as:

$$Kn = \left(\frac{\pi}{6}\right)^{1/2} \frac{\tau - 0.5}{N_{pore}}, \tag{4}$$

Where, $N_{pore}$—lattice number used to discretize the dominant pore size.

See Y. H. Qian, D. dHumieres, and P. Lallemand. Lattice bgk models for navier-stokes equation. Europhysics Letters, 17:479-484, 1992, and Y. H. Zhang, R. S. Qin, and D. R. Emerson Lattice boltzmann simulation of rarefied gas flows in microchannels. *Physical Review E,* 71:047702, 2005, each incorporated herein by reference in their entirety. As described earlier, when τ<0.7, the undesired slippage effect becomes negligible and the computed permeability remains almost unchanged when $N_{pore}$ is greater than 4, which is usually satisfied when scanning rock samples.

Additionally, if τ is decreased to the limit of 0.5, the computed permeability will start to drop due to the undesired inertial effect with the increase of the Reynolds number (Re). See Li et al. (2016). Thus, τ is selected to be τ=0.7 and a small pressure difference is used to reduce the slippage effect and the inertial effect.

As described earlier, a series of high resolution X-ray scans is performed on a set of inspection regions selected outside the set of large porosity regions. Moreover, the set of representative regions is selected from the set of inspection regions to perform the permeability simulations. Each of the set of representative regions is selected to be small in size such that the computational cost of the simulation may be kept at a manageable level. Since each of the set of representative regions is representative of the reservoir carbonate rock, a computed permeability value for a region of the set of representative regions is in the same order of magnitude as a measured permeability value. To ensure that the set of representative regions is representative of the reservoir carbonate rock, a representativeness measure, R, is used.

$$R = (\delta r^2 + \delta \varphi^2)^{1/2}, \quad (5)$$

Where, $$\delta \phi \equiv \frac{\phi - \phi_{ref}}{\phi_{ref}}, \quad (6)$$

$$\delta r \equiv \frac{r - r_{MICP}}{r_{MICP}}, \quad (7)$$

φ—Numerical porosity;
r—pore-throat radius;
$\varphi_{ref}$—reference porosity;
$\varphi_{exp}$—experimental porosity;

Typically, $\varphi_{ref} = \varphi_{exp}$. However, since the corresponding end trim of each of the at least three samples was removed before $\varphi_{exp}$ and $\kappa_{exp}$ were measured, a value of δφ needs to be considered to correspond to $\varphi_{ref} = \varphi_{exp}$. For comparison purposes, δk is defined as:

$$\delta \kappa \equiv \frac{\kappa_{LBM} - \kappa_{exp}}{\kappa_{exp}}, \quad (8)$$

Where,
$\kappa_{LBM}$—the numerical permeability;
$\kappa_{exp}$—the experimental permeability;
The value for R is derived from the empirical correlation (Rezaee et al. and references therein)

$$\kappa \propto \phi^m r^n, \quad (9)$$

Where m and n are constants. See M. R. Rezaee, A. Jafari, and E. Kazemzadeh. Relationships between permeability, porosity and pore throat size in carbonate rocks using regression analysis and neural networks. *Journal of Geophysics and Engineering*, 3:370-367, 2006, incorporated herein by reference in its entirety. With the use of the representativeness measure, the simulations can be conducted utilizing a set of samples that is manageable and yield a reasonable estimate of an absolute permeability. Moreover, since experimental permeability is compared with computed permeability data to determine the absolute permeability, the process of upscaling calculations may be avoided with the method of the present disclosure.

Figure 5:
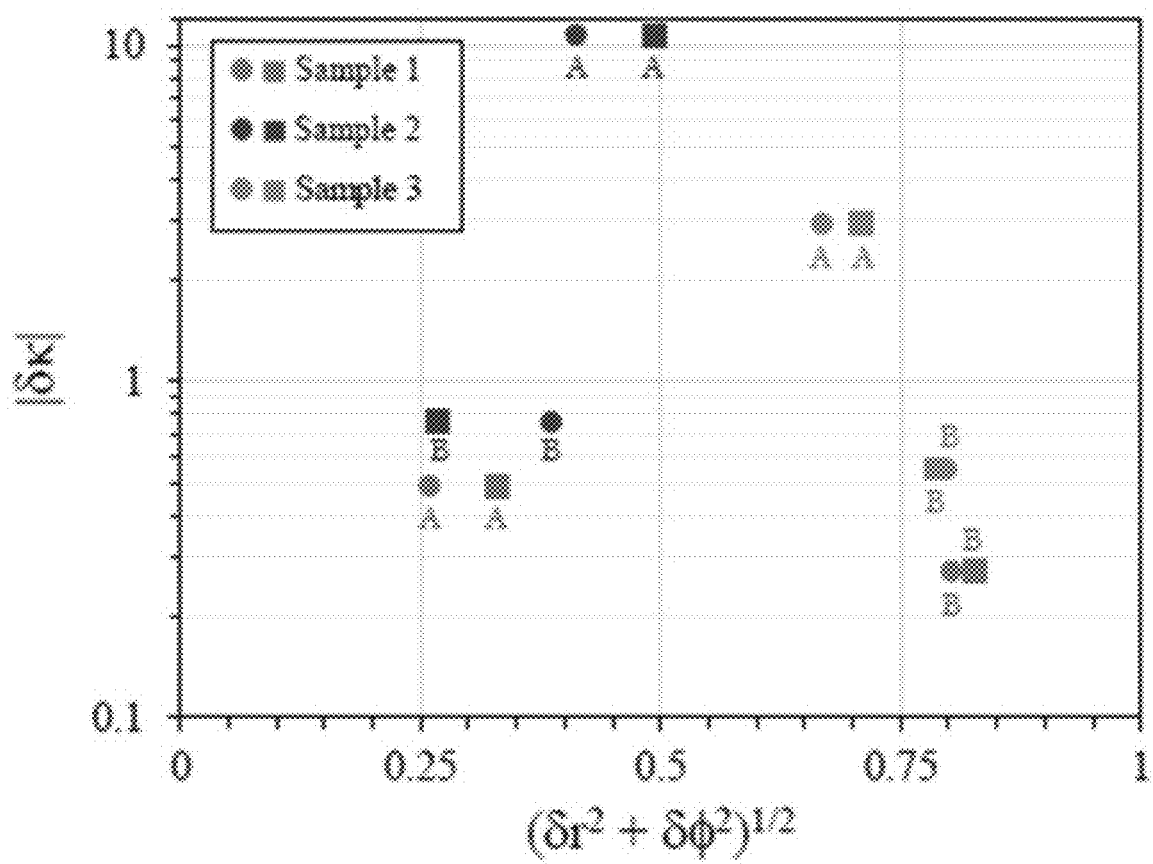
FIG. 5 is a plot of the representativeness measures derived from the permeability results from the LBM computations.

When considering a region selected from the set of inspection regions to be a region of the set of representative regions, regions where R<b is considered, wherein b is an upper bound. The upper bound may be arbitrarily determined or set. When R=1, the error (as estimated by R) corresponds very roughly to a doubling of the permeability. For example, b=1. Permeability is not solely a function of porosity and pore-throat radius. Thus, R may not be the minimum of all regions within the set of representative regions requiring R to be a minimum may not be ideal. FIG. 5 is a graph plotting |δκ| versus R for the six postselected sites, wherein the postselected sites are the set of representative regions.

Table 2 is a summary of the numerical results for the numerical porosity (φ) and the dominant pore-throat radius (r) for the set of representative regions selected from each of the at least three samples. $\kappa_{LBM}$ is the permeability prediction.

TABLE 2

Numerical results. φ and r are the numerical porosity and dominant pore-throat radius of the postselected site, respectively. $\kappa_{LBM}$ is the permeability prediction of our LBM code.

| Sample | Site | Site volume (voxels) | Voxel volume (μm³) | φ (%) | r (μm) | $\kappa_{LBM}$ (mD) |
|---|---|---|---|---|---|---|
| 1 | A | 648³ | 2.53³ | 23.5 | 1.2 | 27.8 |
|   | B | 681³ | 1.55³ | 23.4 | 2.9 | 69.4 |
| 2 | A | 618³ | 0.78³ | 31.5 | 3.7 | 1450 |
|   | B | 649³ | 2.15³ | 21.5 | 7.9 | 216.7 |
| 3 | A | 671³ | 1.53³ | 30.7 | 2.8 | 906.9 |
|   | B | 637³ | 1.53³ | 16.2 | 2.9 | 103.1 |

Table 3 is a comparison of experimental and computed permeabilities, wherein the experimented values were previously shown in table 1 and the computed permeabilities were previously shown in table 2.

TABLE 3

Comparison of experimental and computed permeabilities.

| Sample | Site | δκ (%) |
|---|---|---|
| 1 | A | −49 |
|   | B | +27.3 |
| 2 | A | +1076 |
|   | B | +75.8 |
| 3 | A | +295 |
|   | B | −55 |

The positive values correspond to instances where the numerical code overestimates the permeability, while the negative values correspond to instances where the numerical code underestimates the permeability. As seen in table 3, |δκ| values vary from 27.3% to 1076% with an average of 263% that corresponds to the mean value ($\kappa_{LBM}/\kappa_{exp}$)=3.28.

Figure 4A:
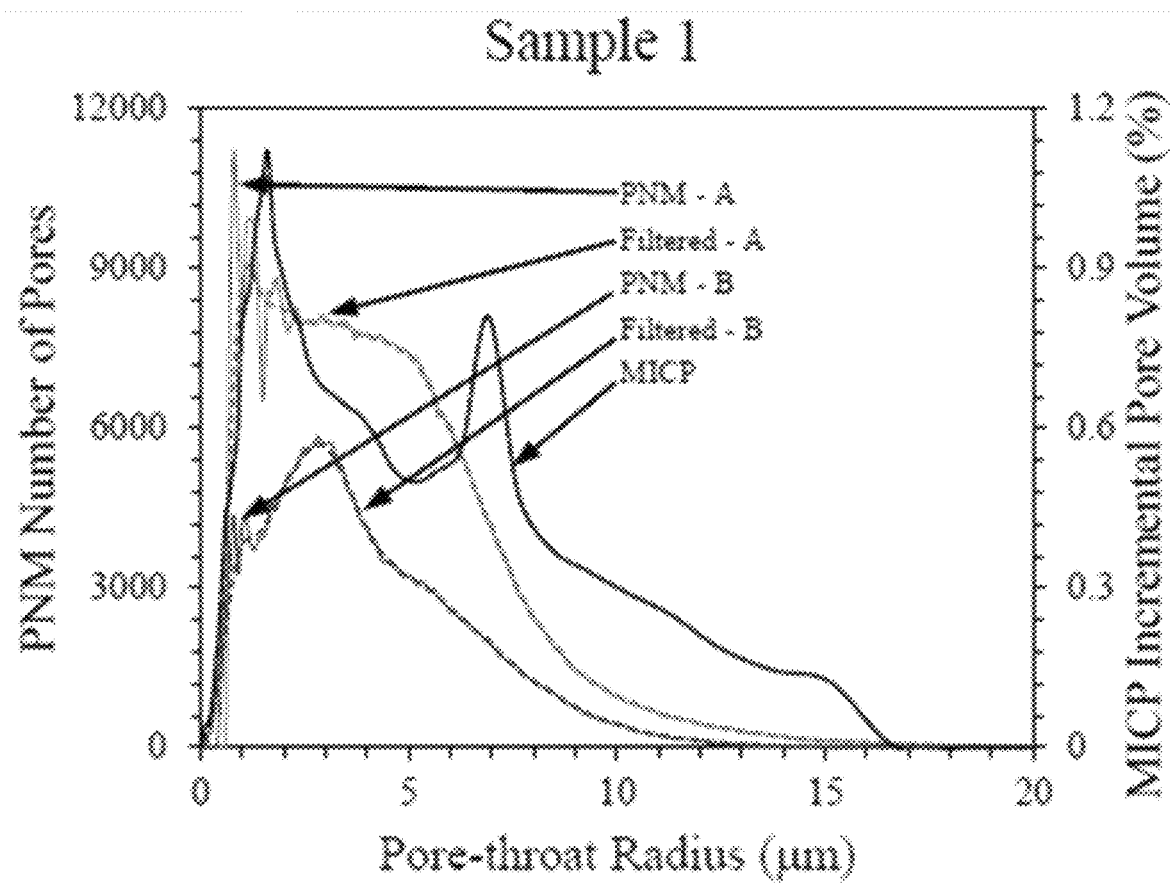
FIG. 4A is a graph illustrating the pore-throat distribution of the first sample from the at least three core samples retrieved from the reservoir carbonate rock.
Figure 4B:
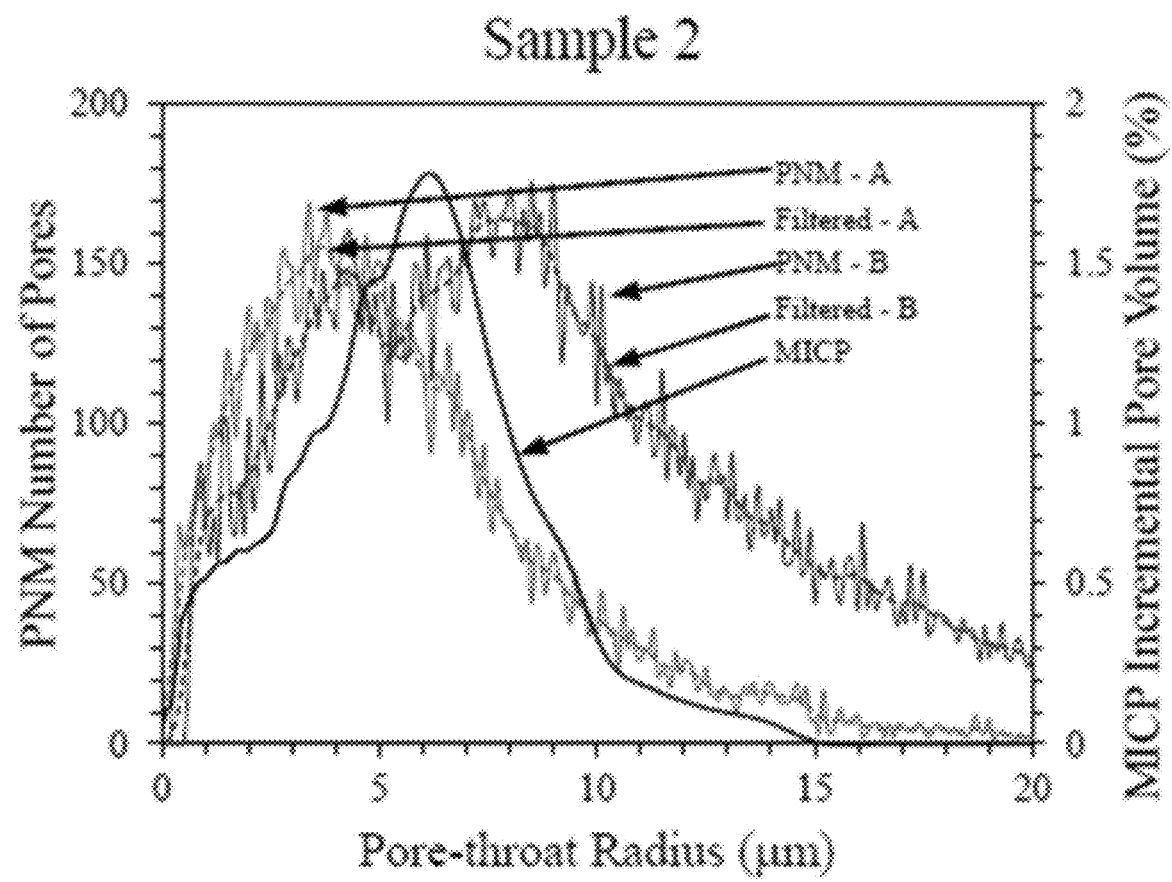
FIG. 4B is a graph illustrating the pore-throat distribution of the second sample from the at least three core samples retrieved from the reservoir carbonate rock.
Figure 4C:
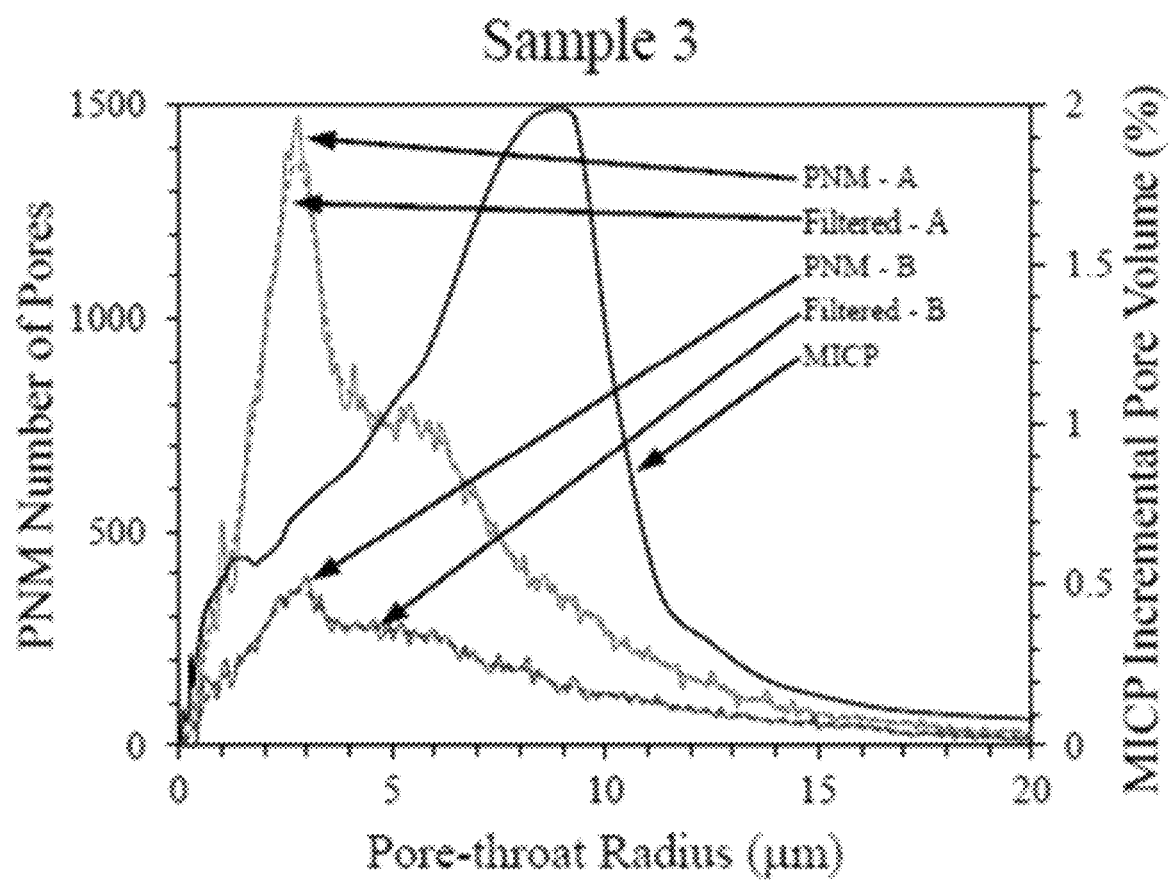
FIG. 4C is a graph illustrating the pore-throat distribution of the third sample from the at least three core samples retrieved from the reservoir carbonate rock.

FIGS. 4A-4C, illustrates the pore-throat radius distribution obtained from the MICP analysis along with the pore-throat radius distribution obtained from the pore-network modelling (PNM) tool in PerGeos software (ThermoFisher Scientific). In other embodiments of the present disclosure, other PNM tools such as Amira-Avizo and OpenPNM may be utilized. In FIGS. 4A-4C, the solid black curves represent MICP data, the blue and red spiky curves represent the PNM data (bin=0.1 μm). To increase the signal-to-noise ratio and simplify the task of determining the dominant pore-throat radius, a Gaussian filter with a radius of 5 pixels (i.e., with standard deviation σ=5/2 and full-width-at-half-maximum FWHM=2√(2ln2)σ≈5.9) was applied to the PNM data. The dashed blue and red curves represent the results of this filtering.

Figure 6:
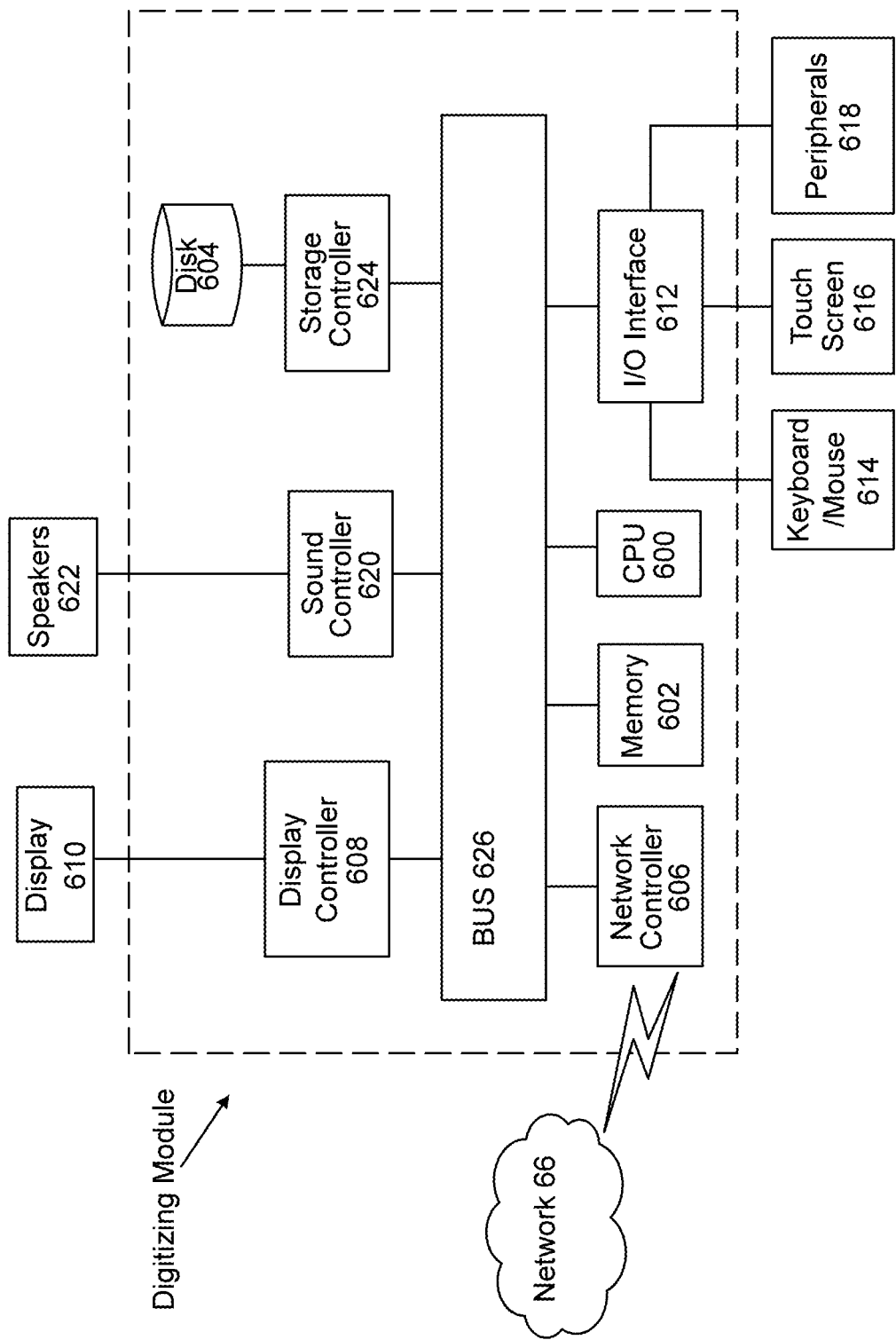
FIG. 6 is a schematic block diagram illustrating a hardware configuration of a digitizing module associated with a digitization process of the method of the present disclosure.

Next, a hardware description of the digitizing module according to exemplary embodiments is described with reference to FIG. 6. In FIG. 6, the digitizing module includes a CPU 600 which performs the processes described above/below. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the digitizing module communicates, such as a server or computer.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple MAC-OS and other systems known to those skilled in the art.

The hardware elements in order to achieve the digitizing module may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The digitizing module in FIG. 6 also includes a network controller 606, such as an Intel Ethernet PRO network interface card from Intel Corporation of America, for interfacing with network 66. As can be appreciated, the network 66 can be a public network, such as the Internet, or a private network such as an LAN or WAN network, or any combination thereof and can also include PSTN or ISDN sub-networks. The network 66 can also be wired, such as an Ethernet network, or can be wireless such as a cellular network including EDGE, 3G and 4G wireless cellular systems. The wireless network can also be WiFi, Bluetooth, or any other wireless form of communication that is known.

The digitizing module further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard.

A sound controller 620 is also provided in the digitizing module, such as Sound Blaster X-Fi Titanium from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the digitizing module. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 7.

Figure 7:
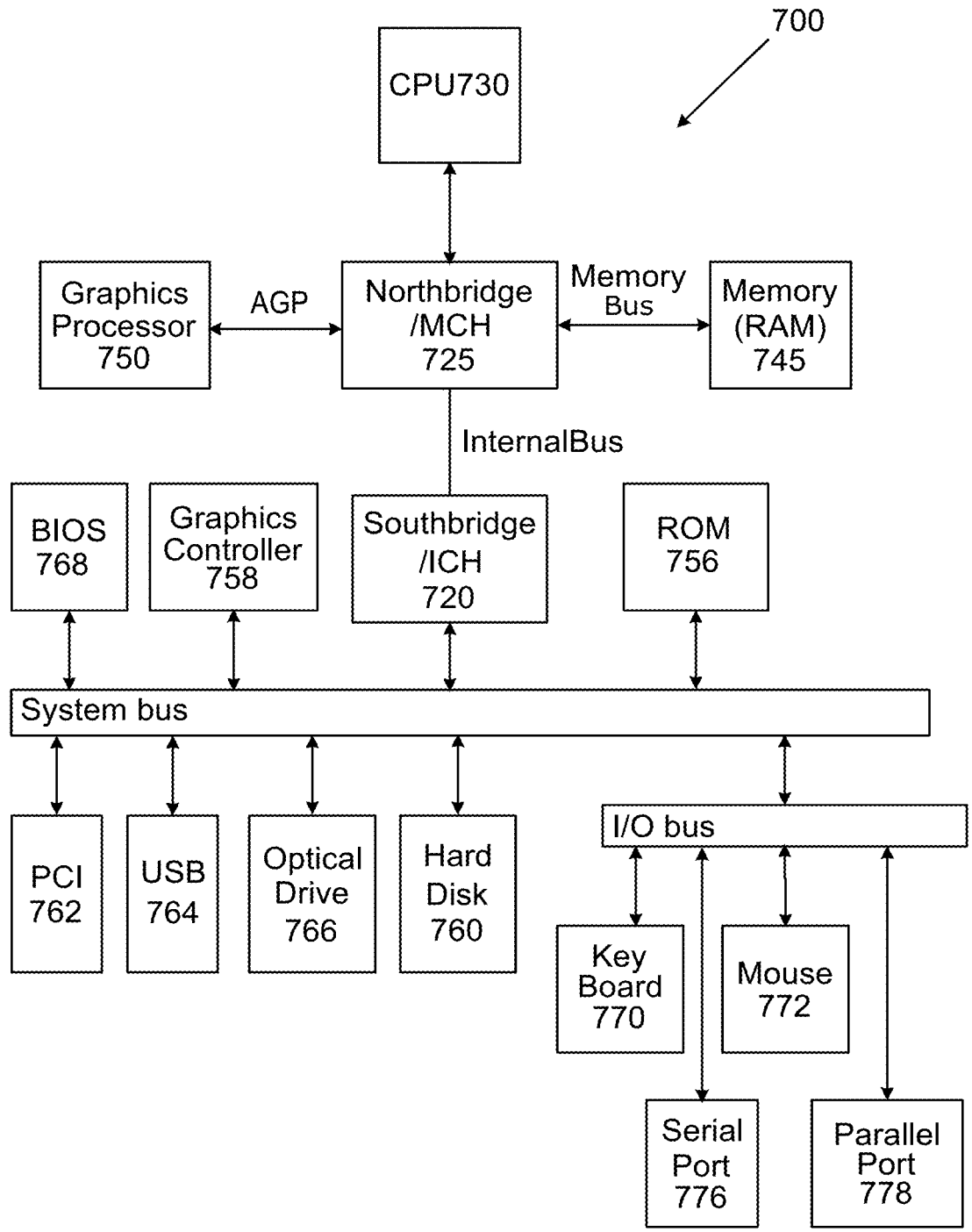
FIG. 7 is a schematic block diagram of a data processing system associated with the digitizing process of the method of the present disclosure.

FIG. 7 shows a schematic diagram of a data processing system, according to certain embodiments, for performing the digitizing process. The data processing system is an example of a computer in which code or instructions implementing the processes of the illustrative embodiments may be located.

In FIG. 7, data processing system 700 employs a hub architecture including a north bridge and memory controller hub (NB/MCH) 725 and a south bridge and input/output (I/O) controller hub (SB/ICH) 720. The central processing unit (CPU) 730 is connected to NB/MCH 725. The NB/MCH 725 also connects to the memory 745 via a memory bus, and connects to the graphics processor 750 via an accelerated graphics port (AGP). The NB/MCH 725 also connects to the SB/ICH 720 via an internal bus (e.g., a unified media interface or a direct media interface). The CPU Processing unit 730 may contain one or more processors and even may be implemented using one or more heterogeneous processor systems.

Figure 8:
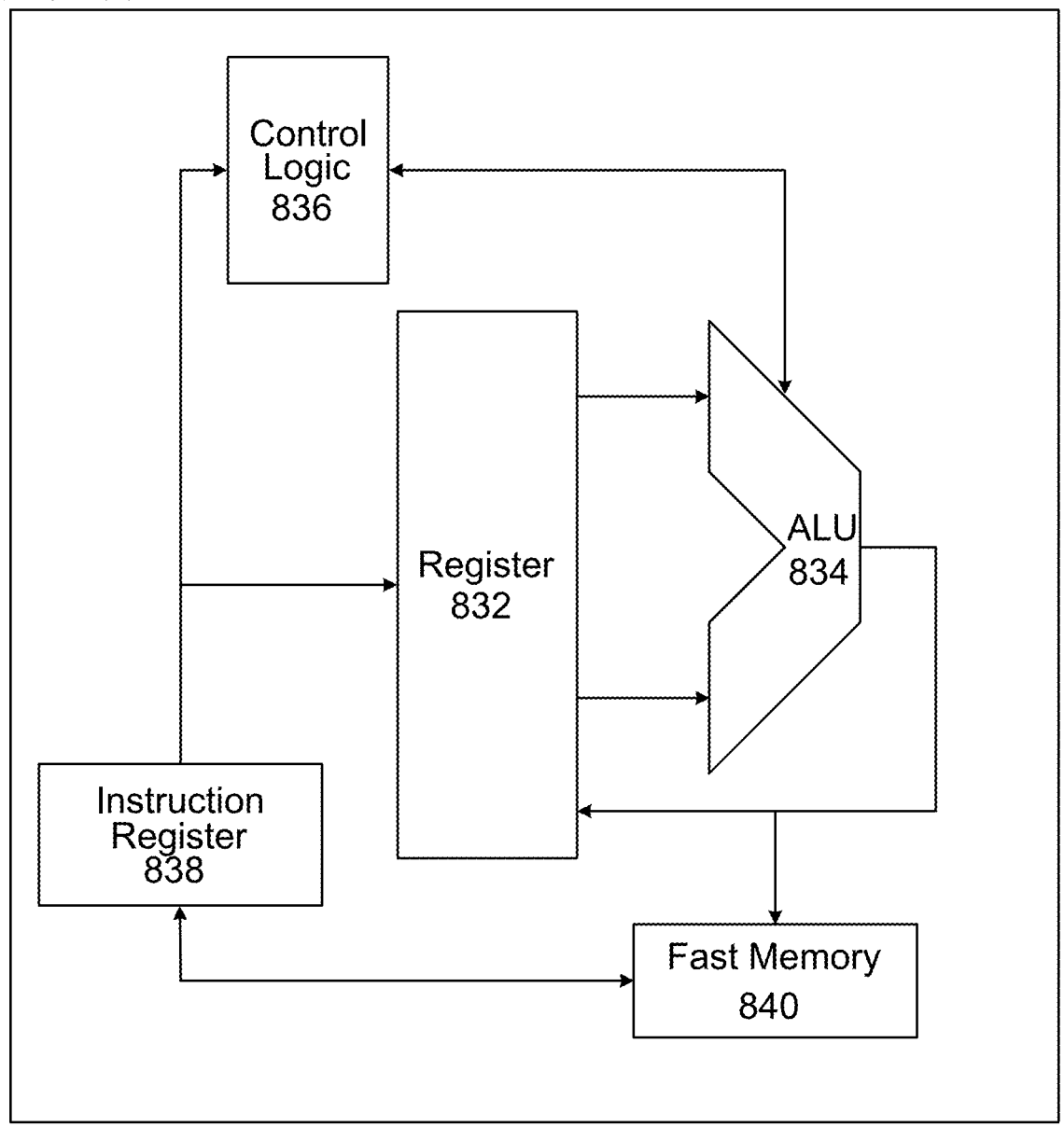
FIG. 8 is a schematic block diagram illustrating one implementation of a central processing unit associated with the digitization process of the method of the present disclosure.

For example, FIG. 8 shows one implementation of CPU 730. In one implementation, the instruction register 838 retrieves instructions from the fast memory 840. At least part of these instructions are fetched from the instruction register 838 by the control logic 836 and interpreted according to the instruction set architecture of the CPU 730. Part of the instructions can also be directed to the register 832. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 834 that loads values from the register 832 and performs logical and mathematical operations on the loaded values according to the instructions. The results from these operations can be feedback into the register and/or stored in the fast memory 840. According to certain implementations, the instruction set architecture of the CPU 730 can use a reduced instruction set architecture, a complex instruction set architecture, a vector processor architecture, a very large instruction word architecture. Furthermore, the CPU 730 can be based on the Von Neuman model or the Harvard model. The CPU 730 can be a digital signal processor, an FPGA, an ASIC, a PLA, a PLD, or a CPLD. Further, the CPU 730 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 7, the data processing system 700 can include that the SB/ICH 720 is coupled through a system bus to an I/O Bus, a read only memory (ROM) 756, universal serial bus (USB) port 764, a flash binary input/output system (BIOS) 768, and a graphics controller 758. PCI/PCIe devices can also be coupled to SB/ICH 720 through a PCI bus 762.

The PCI devices may include, for example, Ethernet adapters, add-in cards, and PC cards for notebook computers. The Hard disk drive 760 and CD-ROM 766 can use, for example, an integrated drive electronics (IDE) or serial advanced technology attachment (SATA) interface. In one implementation the I/O bus can include a super I/O (SIO) device.

Further, the hard disk drive (HDD) 760 and optical drive 766 can also be coupled to the SB/ICH 720 through a system bus. In one implementation, a keyboard 770, a mouse 772, a parallel port 778, and a serial port 776 can be connected to the system bust through the I/O bus. Other peripherals and devices that can be connected to the SB/ICH 720 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 9:
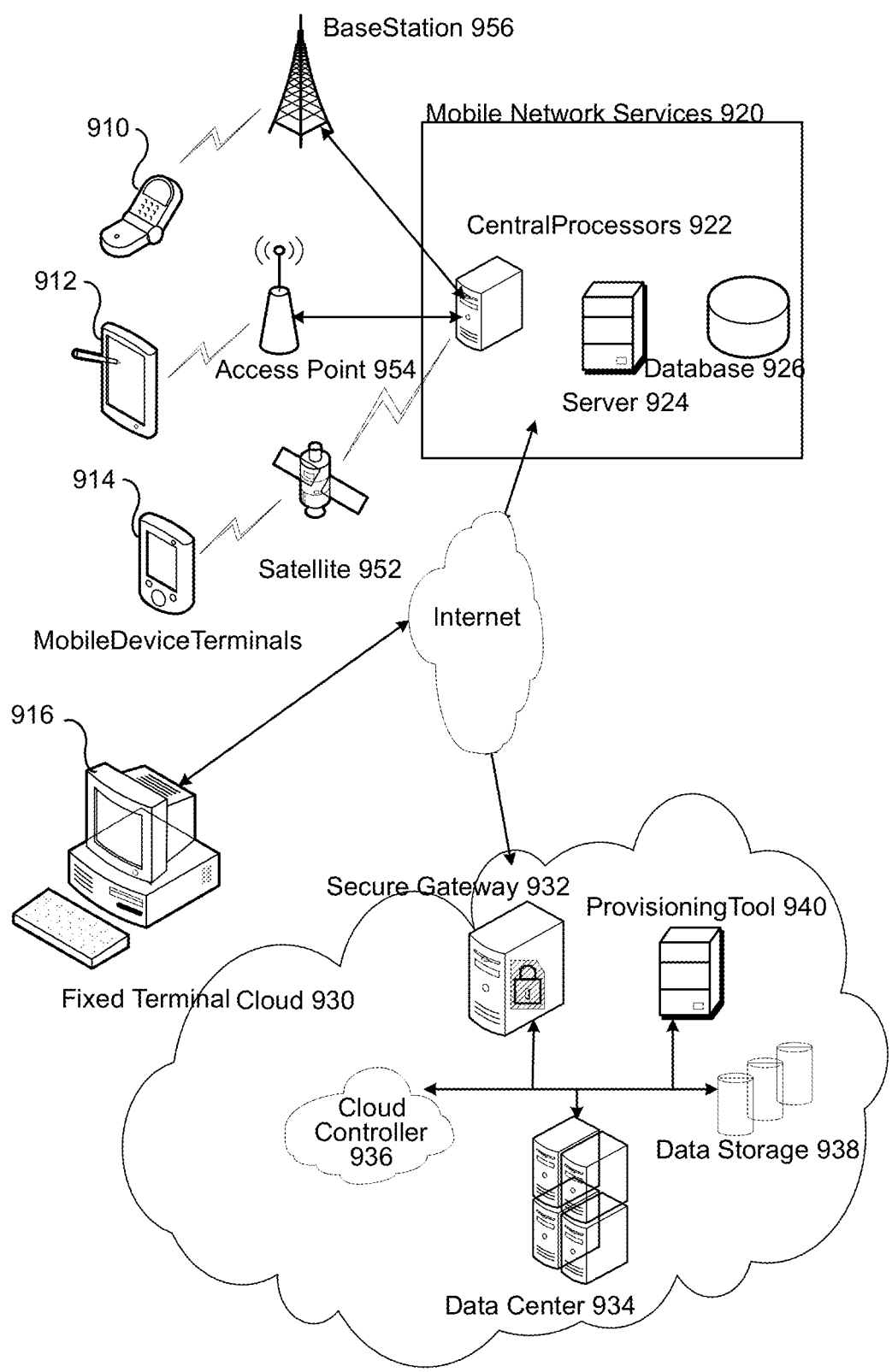
FIG. 9 is a schematic block diagram illustrating the process of utilizing multiple processors distributed across a network for the digitization process.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 9, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s)

or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for determining absolute permeability in carbonates, comprising:
    obtaining at least three core samples of reservoir carbonate rock taken from a set of representative regions of a carbonate rock formation;
    analyzing the at least three core samples to determine a first pore structure for each of the at least three core samples, wherein the first pore structure includes a first pore-body radius distribution and a pore-throat radius distribution, wherein the first pore-body radius distribution is measured with a nuclear magnetic resonance (NMR) analysis and the pore-throat radius distribution is measured with a mercury-injection capillary-pressure (MICP) analysis,
    determining an experimental permeability of each of the at least three core samples, wherein a flow of helium within the first pore structure of each of the at least three core samples is analyzed to determine the experimental permeability of each of the at least three core samples;
    digitizing, using a series of low-resolution X-ray scans, the at least three core samples, then numerically extracting a second pore structure of each of the at least three core samples, wherein the second pore structure includes a second pore-body radius distribution, wherein the digitizing utilizes a binary representation for a rock site and a pore site of each of the at least three core samples;
    comparing the first pore-body radius distribution of the first pore structure and the second pore-body radius distribution of the second pore structure to identify a set of large porosity regions of each of the at least three core samples;
    identifying a set of inspection regions outside the set of large porosity regions for each of the at least three core samples, wherein the set of inspection regions is semi-randomly identified;
    performing a series of high resolution X-ray scans on the set of inspection regions outside the set of large porosity regions for each of the at least three core samples;
    performing numerical modelling on the at least three core samples to determine a computed permeability of each of the at least three core samples; and
    comparing the experimental permeability with the computed permeability to determine an absolute permeability of the reservoir carbonate rock.

2. The method for determining absolute permeability in carbonates as of claim 1, wherein a voxel volume of the series of low resolution X-ray scans is within a range of 25-35 micrometers ($\mu m^3$).

3. The method for determining absolute permeability in carbonates as of claim 1, wherein a voxel volume of the series of high resolution X-ray scans is less than a dominant pore-throat size.

4. The method for determining absolute permeability in carbonates as of claim 1, wherein a mineral composition of each of the at least three core samples is obtained using a quantitative evaluation of minerals by scanning electron microscopy (QEMSCAN).

5. The method for determining absolute permeability in carbonates as of claim 1 further comprising:
    removing a corresponding end trim from each of the at least three core samples;

determining a NMR porosity from the pore-body radius distribution by performing the NMR analysis and the series of low-resolution X-ray scans on the corresponding end trims of each of the at least three core samples, determining a helium porosity and a helium permeability from the pore-throat radius distribution by performing the MICP analysis on a remainder of each of the at least three core samples, and determining the experimental permeability for the reservoir carbonate rock from the NMR porosity, the helium porosity and the helium permeability.

6. The method for determining absolute permeability in carbonates as of claim 5, wherein the corresponding end trim of each of the at least three core samples is cylindrical in shape and has a length within a range of 5 mm-10 mm and a diameter within a range of 20 mm-30 mm.

7. The method for determining absolute permeability in carbonates as of claim 5, wherein the corresponding end trim of each of the at least three core samples is deionized at a pressure ranging from 1250 pounds per square inch (psi)-1750 psi.

8. The method for determining absolute permeability in carbonates as of claim 5, wherein the remainder of each of the at least three core samples is dried, weighed, evacuated, and then immersed in mercury at a preset filling pressure within a range of 1.5 psi-2.0 psi prior to the MICP analysis.

9. The method for determining absolute permeability in carbonates as of claim 1, wherein a resonating frequency of the NMR analysis is within a range of 1.5 megahertz (MHz)-2.5 MHz.

10. The method for determining absolute permeability in carbonates as of claim 1, wherein the series of low resolution X-ray scans has a pixel size within a range of 15 µm-20 µm.

11. The method for determining absolute permeability in carbonates as of claim 1, wherein each of the set of inspection regions has a site volume within a range of 0.8 millimeter$^3$ (mm$^3$)-1.2 mm$^3$.

12. The method for determining absolute permeability in carbonates as of claim 1, wherein the set of representative regions is selected according to a representativeness measure, wherein the representativeness measure is derived as a function of numerical porosity, pore-throat radius, and a reference porosity; and the representativeness measure is lesser than an upper bound.

13. The method for determining absolute permeability in carbonates as of claim 1, computing a difference between the computed permeability and the experimental permeability, wherein the difference is a negative value, if a permeability of the reservoir carbonate rock is underestimated.

14. The method for determining absolute permeability in carbonates as of claim 1, computing a difference between the computed permeability and the experimental permeability, wherein the difference is a positive value, if a permeability of the reservoir carbonate rock is overestimated.

* * * * *